(12) United States Patent
Stals et al.

(10) Patent No.: US 9,150,640 B2
(45) Date of Patent: Oct. 6, 2015

(54) METHOD FOR THE PRODUCTION OF VARIABLE DOMAINS

(75) Inventors: Hilde Stals, Ghent (BE); Veronique De Brabandere, Ghent (BE); Peter Schotte, De Pinte (BE)

(73) Assignee: Ablynx N.V., Zwijnaarde (BE)

( * ) Notice: Subject to any disclaimer, the term of this patent is extended or adjusted under 35 U.S.C. 154(b) by 96 days.

(21) Appl. No.: 13/382,561

(22) PCT Filed: Jul. 9, 2010

(86) PCT No.: PCT/EP2010/004196
§ 371 (c)(1),
(2), (4) Date: Feb. 23, 2012

(87) PCT Pub. No.: WO2011/003622
PCT Pub. Date: Jan. 13, 2011

(65) Prior Publication Data
US 2012/0141460 A1    Jun. 7, 2012

Related U.S. Application Data

(60) Provisional application No. 61/270,613, filed on Jul. 10, 2009.

(51) Int. Cl.
| | | |
|---|---|---|
| *C12P 21/04* | (2006.01) | |
| *C12N 5/00* | (2006.01) | |
| *C12N 5/07* | (2010.01) | |
| *C12N 5/16* | (2006.01) | |
| *C12N 1/12* | (2006.01) | |
| *C07H 21/04* | (2006.01) | |
| *A61K 47/48* | (2006.01) | |
| *C07K 16/00* | (2006.01) | |

(52) U.S. Cl.
CPC ............ *C07K 16/00* (2013.01); *A61K 47/48215* (2013.01); *A61K 47/48338* (2013.01); *C07K 2317/569* (2013.01); *C07K 2319/00* (2013.01)

(58) Field of Classification Search
None
See application file for complete search history.

(56) References Cited

U.S. PATENT DOCUMENTS 8,304,257 B2 * 11/2012 Ackerson et al. ............. 436/525

FOREIGN PATENT DOCUMENTS

| EP | 1 160 255 A1 | 12/2001 |
|---|---|---|
| EP | 1 639 011 A2 | 3/2006 |
| WO | WO 94/25591 A1 | 11/1994 |
| WO | WO 01/94585 A1 | 12/2001 |
| WO | 2004/060965 A2 | 7/2004 |
| WO | WO 2006/003388 A2 | 1/2006 |
| WO | WO 2008/020079 A1 | 2/2008 |
| WO | WO 2008/077945 A2 | 7/2008 |
| WO | WO 2008/101985 A2 | 8/2008 |
| WO | WO 2008/142164 A2 | 11/2008 |
| WO | WO 2009/058383 A2 | 5/2009 |
| WO | WO 2009/068625 A2 | 6/2009 |
| WO | WO 2009/068627 A2 | 6/2009 |

OTHER PUBLICATIONS

Overbeek, 1994, "Factors affecting transgenic animal production," Transgenic animal technology, pp. 96-98.*
Wall, 1996 Theriogenology, vol. 45, pp. 57-68.*
Houdebine, 1994, J. Biotech. vol. 34, pp. 269-287, specifically p. 281.*
Kappell, 1992, Current Opinions in Biotechnology, vol. 3, pp. 548-553.*
Cameron, 1997, Mol. Biol. 7, pp. 253-265.*
Mullins, 1993, Hypotension, vol. 22, pp. 630-633.*
Mullins, 1990, Nature, vol. 344, 541-544.*
Hammer, 1990, Cell, vol. 63, 1099-1112.*
Niemann, 1997, Transg. Res. 7, pp. 73-75.*
Mullins, 1989, EMBO J., vol. 8, pp. 4065-4072.*
Taurog, 1988, J. Immunol., vol. 141, pp. 4020-4023.*
Mullins,1996, J. Clin. Invest. vol. 98, pp. S37-S40.*
Chapman et al., Therapeutic antibody fragments with prolonged in vivo half-lives. Nat Biotechnol. Aug. 1999;17(8):780-3.
Greenwald et al., Poly(ethylene glycol) conjugated drugs and prodrugs: a comprehensive review. Crit Rev Ther Drug Carrier Syst. 2000;17(2):101-61.
Yang et al., Tailoring structure-function and pharmacokinetic properties of single-chain Fv proteins by site-specific PEGylation. Protein Eng. Oct. 2003;16(10):761-70.
Zalipsky, Functionalized poly(ethylene glycol) for preparation of biologically relevant conjugates. Bioconjug Chem. Mar.-Apr. 1995;6(2):150-65.
Chapman, PEGylated antibodies and antibody fragments for improved therapy: a review. Advanced Drug Delivery Reviews. 2002; 54: 531-545.
Veronese et al., Introduction and overview of peptide and protein pegylation. Advanced Drug Delivery Reviews. 2002; 54: 453-456.

* cited by examiner

*Primary Examiner* — Hong Sang
(74) *Attorney, Agent, or Firm* — Wolf, Greenfield & Sacks, P.C.

(57) ABSTRACT

The present invention provides methods for the expression and/or production of variable domains with a C-terminal extension that can be used for coupling of the variable domain to one or more further groups, residues or moieties. In the method of the invention a yield of at least 80% of variable domains with a cysteine containing C-terminal extension is obtained. Also variable domains are provided and polypeptides comprising one or more variable domains obtainable by the methods of the present invention, as well as compounds that comprise such variable domains and/or polypeptides coupled to one or more groups, residues or moieties.

16 Claims, 10 Drawing Sheets

SEQUENCE LISTING

<160> NUMBER OF SEQ ID NOS: 27

<210> SEQ ID NO 1
<211> LENGTH: 4
<212> TYPE: PRT
<213> ORGANISM: Artificial Sequence
<220> FEATURE:
<223> OTHER INFORMATION: Linker sequence

<400> SEQUENCE: 1

Gly Gly Gly Cys
1

<210> SEQ ID NO 2
<211> LENGTH: 5
<212> TYPE: PRT
<213> ORGANISM: Artificial Sequence
<220> FEATURE:
<223> OTHER INFORMATION: Linker sequence

<400> SEQUENCE: 2

Gly Gly Gly Cys Gly
1               5

<210> SEQ ID NO 3
<211> LENGTH: 3
<212> TYPE: PRT
<213> ORGANISM: Artificial Sequence
<220> FEATURE:
<223> OTHER INFORMATION: Linker sequence

<400> SEQUENCE: 3

Gly Gly Cys
1

```
<210> SEQ ID NO 4
<211> LENGTH: 2
<212> TYPE: PRT
<213> ORGANISM: Artificial Sequence
<220> FEATURE:
<223> OTHER INFORMATION: Linker sequence

<400> SEQUENCE: 4

Gly Cys
1

<210> SEQ ID NO 5
<211> LENGTH: 1
<212> TYPE: PRT
<213> ORGANISM: Artificial Sequence
<220> FEATURE:
<223> OTHER INFORMATION: Linker sequence

<400> SEQUENCE: 5

Cys
1

<210> SEQ ID NO 6
<211> LENGTH: 2
<212> TYPE: PRT
<213> ORGANISM: Artificial Sequence
<220> FEATURE:
<223> OTHER INFORMATION: Linker sequence

<400> SEQUENCE: 6

Cys Gly
1

<210> SEQ ID NO 7
<211> LENGTH: 4
<212> TYPE: PRT
<213> ORGANISM: Artificial Sequence
<220> FEATURE:
<223> OTHER INFORMATION: Linker sequence

<400> SEQUENCE: 7

Ala Ala Ala Cys
1

<210> SEQ ID NO 8
<211> LENGTH: 5
<212> TYPE: PRT
<213> ORGANISM: Artificial Sequence
<220> FEATURE:
<223> OTHER INFORMATION: Linker sequence

<400> SEQUENCE: 8

Val Thr Val Ser Cys
1               5

<210> SEQ ID NO 9
<211> LENGTH: 288
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30
```

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
     50                  55                  60

Arg Thr Tyr Tyr Ala Asp Ser Val Lys Gly Arg Phe Thr Ile Ser Arg
 65                  70                  75                  80

Asp Asn Ser Lys Lys Thr Leu Tyr Leu Gln Met Asn Ser Leu Arg Pro
                 85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
            115                 120                 125

Gly Ser Gly Gly Gly Ser Gly Gly Gly Ser Gly Gly Gly Gly
            130                 135                 140

Ser Gly Gly Gly Gly Ser Gly Gly Gly Gly Ser Gly Gly Gly Gly Ser
145                 150                 155                 160

Glu Val Gln Leu Leu Glu Ser Gly Gly Leu Val Gln Pro Gly Gly
                165                 170                 175

Ser Leu Arg Leu Ser Cys Ala Ala Ser Gly Leu Pro Phe Ser Thr Lys
            180                 185                 190

Ser Met Gly Trp Phe Arg Gln Ala Pro Gly Lys Gly Arg Glu Phe Val
            195                 200                 205

Ser Arg Ile Ser Pro Gly Gly Thr Ser Arg Tyr Tyr Gly Asp Phe Val
            210                 215                 220

Lys Gly Arg Phe Thr Ile Ser Arg Asp Asn Lys Asn Thr Leu Tyr
225                 230                 235                 240

Leu Gln Met Asn Ser Leu Arg Ala Glu Asp Thr Ala Val Tyr Tyr Cys
                245                 250                 255

Ala Ser Gly Glu Arg Ser Thr Tyr Ile Gly Ser Asn Tyr Tyr Arg Thr
            260                 265                 270

Asn Glu Tyr Asp Tyr Trp Gly Gln Gly Thr Leu Val Thr Val Ser Ser
            275                 280                 285

<210> SEQ ID NO 10
<211> LENGTH: 292
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
     50                  55                  60

Arg Thr Tyr Tyr Ala Asp Ser Val Lys Gly Arg Phe Thr Ile Ser Arg
 65                  70                  75                  80

Asp Asn Ser Lys Lys Thr Leu Tyr Leu Gln Met Asn Ser Leu Arg Pro
                 85                  90                  95

Glu Asp Thr Ala Val Tyr Tyr Cys Gln Thr Ser Gly Ser Gly Ser Pro
            100                 105                 110

```
Asn Phe Trp Gly Gln Gly Thr Leu Val Thr Val Ser Ser Gly Gly Gly
            115                 120                 125

Gly Ser Gly Gly Gly Gly Ser Gly Gly Gly Gly Ser Gly Gly Gly Gly
        130                 135                 140

Ser Gly Gly Gly Gly Ser Gly Gly Gly Gly Ser Gly Gly Gly Gly Ser
145                 150                 155                 160

Glu Val Gln Leu Leu Glu Ser Gly Gly Leu Val Gln Pro Gly Gly
                165                 170                 175

Ser Leu Arg Leu Ser Cys Ala Ala Ser Gly Leu Pro Phe Ser Thr Lys
            180                 185                 190

Ser Met Gly Trp Phe Arg Gln Ala Pro Gly Lys Gly Arg Glu Phe Val
            195                 200                 205

Ser Arg Ile Ser Pro Gly Gly Thr Ser Arg Tyr Tyr Gly Asp Phe Val
            210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
                245                 250                 255

Ala Ser Gly Glu Arg Ser Thr Tyr Ile Gly Ser Asn Tyr Tyr Arg Thr
            260                 265                 270

Asn Glu Tyr Asp Tyr Trp Gly Gln Gly Thr Leu Val Thr Val Ser Ser
            275                 280                 285

Gly Gly Gly Cys
        290

<210> SEQ ID NO 11
<211> LENGTH: 293
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
        50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Gly Ser Gly Ser Pro
            100                 105                 110

Asn Phe Trp Gly Gln Gly Thr Leu Val Thr Val Ser Ser Gly Gly Gly
            115                 120                 125

Gly Ser Gly Gly Gly Gly Ser Gly Gly Gly Gly Ser Gly Gly Gly Gly
        130                 135                 140

Ser Gly Gly Gly Gly Ser Gly Gly Gly Gly Ser Gly Gly Gly Gly Ser
145                 150                 155                 160

Glu Val Gln Leu Leu Glu Ser Gly Gly Gly Leu Val Gln Pro Gly Gly
                165                 170                 175
```

```
Ser Leu Arg Leu Ser Cys Ala Ala Ser Gly Leu Pro Phe Ser Thr Lys
            180                 185                 190

Ser Met Gly Trp Phe Arg Gln Ala Pro Gly Lys Gly Arg Glu Phe Val
            195                 200                 205

Ser Arg Ile Ser Pro Gly Gly Thr Ser Arg Tyr Tyr Gly Asp Phe Val
            210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
            245                 250                 255

Ala Ser Gly Glu Arg Ser Thr Tyr Ile Gly Ser Asn Tyr Tyr Arg Thr
            260                 265                 270

Asn Glu Tyr Asp Tyr Trp Gly Gln Gly Thr Leu Val Thr Val Ser Ser
            275                 280                 285

Gly Gly Gly Cys Gly
            290

<210> SEQ ID NO 12
<211> LENGTH: 291
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
            50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
            85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
            115                 120                 125

Gly Ser Gly Gly Gly Gly Ser Gly Gly Gly Gly Ser Gly Gly Gly Gly
            130                 135                 140

Ser Gly Gly Gly Gly Ser Gly Gly Gly Gly Ser Gly Gly Gly Gly Ser
145                 150                 155                 160

Glu Val Gln Leu Leu Glu Ser Gly Gly Gly Leu Val Gln Pro Gly Gly
            165                 170                 175

Ser Leu Arg Leu Ser Cys Ala Ala Ser Gly Leu Pro Phe Ser Thr Lys
            180                 185                 190

Ser Met Gly Trp Phe Arg Gln Ala Pro Gly Lys Gly Arg Glu Phe Val
            195                 200                 205

Ser Arg Ile Ser Pro Gly Gly Thr Ser Arg Tyr Tyr Gly Asp Phe Val
            210                 215                 220

Lys Gly Arg Phe Thr Ile Ser Arg Asp Asn Ser Lys Asn Thr Leu Tyr
225                 230                 235                 240
```

```
Leu Gln Met Asn Ser Leu Arg Ala Glu Asp Thr Ala Val Tyr Tyr Cys
                245                 250                 255

Ala Ser Gly Glu Arg Ser Thr Tyr Ile Gly Ser Asn Tyr Tyr Arg Thr
            260                 265                 270

Asn Glu Tyr Asp Tyr Trp Gly Gln Gly Thr Leu Val Thr Val Ser Ser
        275                 280                 285

Gly Gly Cys
    290

<210> SEQ ID NO 13
<211> LENGTH: 290
<212> TYPE: PRT
<213> ORGANISM: Artificial Sequence
<220> FEATURE:
<223> OTHER INFORMATION: Nanobody sequence

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Glu Val Gln Leu Leu Glu Ser Gly Gly Gly Leu Val Gln Pro Gly Gly
                165                 170                 175

Ser Leu Arg Leu Ser Cys Ala Ala Ser Gly Leu Pro Phe Ser Thr Lys
            180                 185                 190

Ser Met Gly Trp Phe Arg Gln Ala Pro Gly Lys Gly Arg Glu Phe Val
        195                 200                 205

Ser Arg Ile Ser Pro Gly Gly Thr Ser Arg Tyr Tyr Gly Asp Phe Val
    210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
                245                 250                 255

Ala Ser Gly Glu Arg Ser Thr Tyr Ile Gly Ser Asn Tyr Tyr Arg Thr
            260                 265                 270

Asn Glu Tyr Asp Tyr Trp Gly Gln Gly Thr Leu Val Thr Val Ser Ser
        275                 280                 285

Gly Cys
    290
```

<210> SEQ ID NO 14
<211> LENGTH: 289
<212> TYPE: PRT
<213> ORGANISM: Artificial Sequence
<220> FEATURE:
<223> OTHER INFORMATION: Nanobody sequence

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Glu Val Gln Leu Leu Glu Ser Gly Gly Gly Leu Val Gln Pro Gly Gly
                165                 170                 175

Ser Leu Arg Leu Ser Cys Ala Ala Ser Gly Leu Pro Phe Ser Thr Lys
            180                 185                 190

Ser Met Gly Trp Phe Arg Gln Ala Pro Gly Lys Gly Arg Glu Phe Val
        195                 200                 205

Ser Arg Ile Ser Pro Gly Gly Thr Ser Arg Tyr Tyr Gly Asp Phe Val
    210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
                245                 250                 255

Ala Ser Gly Glu Arg Ser Thr Tyr Ile Gly Ser Asn Tyr Tyr Arg Thr
            260                 265                 270

Asn Glu Tyr Asp Tyr Trp Gly Gln Gly Thr Leu Val Thr Val Ser Ser
        275                 280                 285

Cys
```

<210> SEQ ID NO 15
<211> LENGTH: 290
<212> TYPE: PRT
<213> ORGANISM: Artificial Sequence
<220> FEATURE:
<223> OTHER INFORMATION: Nanobody sequence

<400> SEQUENCE: 15

```
Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
            50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
            115                 120                 125

Gly Ser Gly Gly Gly Gly Ser Gly Gly Gly Ser Gly Gly Gly Gly
            130                 135                 140

Ser Gly Gly Gly Gly Ser Gly Gly Gly Ser Gly Gly Gly Gly Ser
145                 150                 155                 160

Glu Val Gln Leu Leu Glu Ser Gly Gly Leu Val Gln Pro Gly Gly
                165                 170                 175

Ser Leu Arg Leu Ser Cys Ala Ala Ser Gly Leu Pro Phe Ser Thr Lys
            180                 185                 190

Ser Met Gly Trp Phe Arg Gln Ala Pro Gly Lys Gly Arg Glu Phe Val
            195                 200                 205

Ser Arg Ile Ser Pro Gly Gly Thr Ser Arg Tyr Tyr Gly Asp Phe Val
            210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
                245                 250                 255

Ala Ser Gly Glu Arg Ser Thr Tyr Ile Gly Ser Asn Tyr Tyr Arg Thr
            260                 265                 270

Asn Glu Tyr Asp Tyr Trp Gly Gln Gly Thr Leu Val Thr Val Ser Ser
            275                 280                 285

Cys Gly
    290

<210> SEQ ID NO 16
<211> LENGTH: 292
<212> TYPE: PRT
<213> ORGANISM: Artificial Sequence
<220> FEATURE:
<223> OTHER INFORMATION: Nanobody sequence

<400> SEQUENCE: 16

Glu Val Gln Leu Leu Glu Ser Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
            50                  55                  60

Arg Thr Tyr Tyr Ala Asp Ser Val Lys Gly Arg Phe Thr Ile Ser Arg
65                  70                  75                  80

```
Asp Asn Ser Lys Lys Thr Leu Tyr Leu Gln Met Asn Ser Leu Arg Pro
             85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Gly Ser Gly Gly Gly Ser Gly Gly Gly Gly
    130                 135                 140

Ser Gly Gly Gly Gly Ser Gly Gly Gly Ser Gly Gly Gly Gly Ser
145                 150                 155                 160

Glu Val Gln Leu Leu Glu Ser Gly Gly Leu Val Gln Pro Gly Gly
                165                 170                 175

Ser Leu Arg Leu Ser Cys Ala Ala Ser Gly Leu Pro Phe Ser Thr Lys
            180                 185                 190

Ser Met Gly Trp Phe Arg Gln Ala Pro Gly Lys Gly Arg Glu Phe Val
            195                 200                 205

Ser Arg Ile Ser Pro Gly Gly Thr Ser Arg Tyr Tyr Gly Asp Phe Val
            210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
            245                 250                 255

Ala Ser Gly Glu Arg Ser Thr Tyr Ile Gly Ser Asn Tyr Tyr Arg Thr
            260                 265                 270

Asn Glu Tyr Asp Tyr Trp Gly Gln Gly Thr Leu Val Thr Val Ser Ser
            275                 280                 285

Ala Ala Ala Cys
            290

<210> SEQ ID NO 17
<211> LENGTH: 288
<212> TYPE: PRT
<213> ORGANISM: Artificial Sequence
<220> FEATURE:
<223> OTHER INFORMATION: Nanobody sequence

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
        50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
            85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Gly Ser Gly Gly Gly Ser Gly Gly Gly Gly
    130                 135                 140
```

-continued

```
Ser Gly Gly Gly Gly Ser Gly Gly Gly Ser Gly Gly Gly Ser
145                 150                 155                 160

Glu Val Gln Leu Leu Glu Ser Gly Gly Gly Leu Val Gln Pro Gly Gly
                165                 170                 175

Ser Leu Arg Leu Ser Cys Ala Ala Ser Gly Leu Pro Phe Ser Thr Lys
        180                 185                 190

Ser Met Gly Trp Phe Arg Gln Ala Pro Gly Lys Gly Arg Glu Phe Val
    195                 200                 205

Ser Arg Ile Ser Pro Gly Gly Thr Ser Arg Tyr Tyr Gly Asp Phe Val
    210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
                245                 250                 255

Ala Ser Gly Glu Arg Ser Thr Tyr Ile Gly Ser Asn Tyr Tyr Arg Thr
            260                 265                 270

Asn Glu Tyr Asp Tyr Trp Gly Gln Gly Thr Leu Val Thr Val Ser Cys
        275                 280                 285

<210> SEQ ID NO 18
<211> LENGTH: 259
<212> TYPE: PRT
<213> ORGANISM: Artificial Sequence
<220> FEATURE:
<223> OTHER INFORMATION: Nanobody sequence

<400> SEQUENCE: 18

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
    50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Glu Ser Val Glu Gly Arg Phe Thr Ile Ser Arg Asp Asn Ala Lys Arg
        195                 200                 205

Thr Val Tyr Leu Gln Met Asn Ser Leu Arg Ala Glu Asp Thr Ala Val
    210                 215                 220
```

```
Tyr Tyr Cys Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser

<210> SEQ ID NO 19
<211> LENGTH: 263
<212> TYPE: PRT
<213> ORGANISM: Artificial Sequence
<220> FEATURE:
<223> OTHER INFORMATION: Nanobody sequence

<400> SEQUENCE: 19

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
    50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Glu Ser Val Glu Gly Arg Phe Thr Ile Ser Arg Asp Asn Ala Lys Arg
        195                 200                 205

Thr Val Tyr Leu Gln Met Asn Ser Leu Arg Ala Glu Asp Thr Ala Val
    210                 215                 220

Tyr Tyr Cys Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Gly Gly Gly Cys
            260

<210> SEQ ID NO 20
<211> LENGTH: 264
<212> TYPE: PRT
<213> ORGANISM: Artificial Sequence
<220> FEATURE:
<223> OTHER INFORMATION: Nanobody sequence

<400> SEQUENCE: 20
```

-continued

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
    50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Glu Ser Val Glu Gly Arg Phe Thr Ile Ser Arg Asp Asn Ala Lys Arg
        195                 200                 205

Thr Val Tyr Leu Gln Met Asn Ser Leu Arg Ala Glu Asp Thr Ala Val
    210                 215                 220

Tyr Tyr Cys Ala Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Gly Gly Gly Cys Gly
            260

<210> SEQ ID NO 21
<211> LENGTH: 262
<212> TYPE: PRT
<213> ORGANISM: Artificial Sequence
<220> FEATURE:
<223> OTHER INFORMATION: Nanobody sequence

<400> SEQUENCE: 21

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Ser Thr Tyr Tyr Pro Glu Ser Val
    50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
                85                  90                  95

```
Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
            130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Glu Ser Val Glu Gly Arg Phe Thr Ile Ser Arg Asp Asn Ala Lys Arg
            195                 200                 205

Thr Val Tyr Leu Gln Met Asn Ser Leu Arg Ala Glu Asp Thr Ala Val
            210                 215                 220

Tyr Tyr Cys Ala Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Gly Gly Cys
            260
```

<210> SEQ ID NO 22
<211> LENGTH: 261
<212> TYPE: PRT
<213> ORGANISM: Artificial Sequence
<220> FEATURE:
<223> OTHER INFORMATION: Nanobody sequence

<400> SEQUENCE: 22

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
    50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
            115                 120                 125

Ala Ala Ala Glu Val Gln Leu Val Glu Ser Gly Gly Gly Leu Val Gln
            130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190
```

```
Glu Ser Val Glu Gly Arg Phe Thr Ile Ser Arg Asp Asn Ala Lys Arg
            195                 200                 205

Thr Val Tyr Leu Gln Met Asn Ser Leu Arg Ala Glu Asp Thr Ala Val
            210                 215                 220

Tyr Tyr Cys Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Gly Cys
            260

<210> SEQ ID NO 23
<211> LENGTH: 260
<212> TYPE: PRT
<213> ORGANISM: Artificial Sequence
<220> FEATURE:
<223> OTHER INFORMATION: Nanobody sequence

<400> SEQUENCE: 23

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
    50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Glu Ser Val Glu Gly Arg Phe Thr Ile Ser Arg Asp Asn Ala Lys Arg
        195                 200                 205

Thr Val Tyr Leu Gln Met Asn Ser Leu Arg Ala Glu Asp Thr Ala Val
    210                 215                 220

Tyr Tyr Cys Ala Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Cys
            260

<210> SEQ ID NO 24
```

```
<211> LENGTH: 261
<212> TYPE: PRT
<213> ORGANISM: Artificial Sequence
<220> FEATURE:
<223> OTHER INFORMATION: Nanobody sequence

<400> SEQUENCE: 24

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
    50                  55                  60

Glu Gly Arg Phe Thr Ile Ser Arg Asp Asn Ala Lys Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Glu Ser Val Glu Gly Arg Phe Thr Ile Ser Arg Asp Asn Ala Lys Arg
        195                 200                 205

Thr Val Tyr Leu Gln Met Asn Ser Leu Arg Ala Glu Asp Thr Ala Val
    210                 215                 220

Tyr Tyr Cys Ala Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Cys Gly
            260

<210> SEQ ID NO 25
<211> LENGTH: 263
<212> TYPE: PRT
<213> ORGANISM: Artificial Sequence
<220> FEATURE:
<223> OTHER INFORMATION: Nanobody sequence

<400> SEQUENCE: 25

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
```

```
            50                  55                  60
Glu Gly Arg Phe Thr Ile Ser Arg Asp Asn Ala Lys Arg Thr Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Gln Gly Arg Val Arg Thr Leu Pro
                100                 105                 110

Ser Glu Tyr Thr Phe Trp Gly Gln Gly Thr Gln Val Thr Val Ser Ser
                115                 120                 125

Ala Ala Ala Glu Val Gln Leu Val Glu Ser Gly Gly Gly Leu Val Gln
                130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
                180                 185                 190

Glu Ser Val Glu Gly Arg Phe Thr Ile Ser Arg Asp Asn Ala Lys Arg
                195                 200                 205

Thr Val Tyr Leu Gln Met Asn Ser Leu Arg Ala Glu Asp Thr Ala Val
                210                 215                 220

Tyr Tyr Cys Ala Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Ala Ala Ala Cys
                260

<210> SEQ ID NO 26
<211> LENGTH: 261
<212> TYPE: PRT
<213> ORGANISM: Artificial Sequence
<220> FEATURE:
<223> OTHER INFORMATION: Nanobody sequence

<400> SEQUENCE: 26

Asp Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Tyr Asn
                 20                  25                  30

Pro Met Gly Trp Phe Arg Gln Ala Pro Gly Lys Gly Arg Glu Leu Val
                 35                  40                  45

Ala Ala Ile Ser Arg Thr Gly Gly Ser Thr Tyr Tyr Pro Glu Ser Val
                 50                  55                  60

Glu Gly Arg Phe Thr Ile Ser Arg Asp Asn Ala Lys Arg Thr Val Tyr
 65                  70                  75                  80

Leu Gln Met Asn Ser Leu Arg Ala Glu Asp Thr Ala Val Tyr Tyr Cys
                 85                  90                  95

Ala Ala Ala Gly Val Arg Ala Glu Gln Gly Arg Val Arg Thr Leu Pro
                100                 105                 110

Ser Glu Tyr Thr Phe Trp Gly Gln Gly Thr Gln Val Thr Val Ser Ser
                115                 120                 125

Ala Ala Ala Glu Val Gln Leu Val Glu Ser Gly Gly Gly Leu Val Gln
                130                 135                 140

Pro Gly Gly Ser Leu Arg Leu Ser Cys Ala Ala Ser Gly Arg Thr Phe
```

```
                145                 150                 155                 160
Ser Tyr Asn Pro Met Gly Trp Phe Arg Gln Ala Pro Gly Lys Gly Arg
                    165                 170                 175

Glu Leu Val Ala Ala Ile Ser Arg Thr Gly Gly Ser Thr Tyr Tyr Pro
                180                 185                 190

Glu Ser Val Glu Gly Arg Phe Thr Ile Ser Arg Asp Asn Ala Lys Arg
            195                 200                 205

Thr Val Tyr Leu Gln Met Asn Ser Leu Arg Ala Glu Asp Thr Ala Val
    210                 215                 220

Tyr Tyr Cys Ala Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Thr Val Ser Cys
                260

<210> SEQ ID NO 27
<211> LENGTH: 292
<212> TYPE: PRT
<213> ORGANISM: Artificial Sequence
<220> FEATURE:
<223> OTHER INFORMATION: Nanobody sequence

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Gly Gly Gly Gly Ser
145                 150                 155                 160

Glu Val Gln Leu Leu Glu Ser Gly Gly Gly Leu Val Gln Pro Gly Gly
                165                 170                 175

Ser Leu Arg Leu Ser Cys Ala Ala Ser Gly Leu Pro Phe Ser Thr Lys
            180                 185                 190

Ser Met Gly Trp Phe Arg Gln Ala Pro Gly Lys Gly Arg Glu Phe Val
        195                 200                 205

Ser Arg Ile Ser Pro Gly Gly Thr Ser Arg Tyr Tyr Gly Asp Phe Val
    210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Ala Glu Asp Thr Ala Val Tyr Tyr Cys
```

```
                        245                 250                 255
Ala Ser Gly Glu Arg Ser Thr Tyr Ile Gly Ser Asn Tyr Tyr Arg Thr
                260                 265                 270

Asn Glu Tyr Asp Tyr Trp Gly Gln Gly Thr Leu Val Thr Val Ser Ser
            275                 280                 285

Gly Gly Gly Ser
        290
```

METHOD FOR THE PRODUCTION OF VARIABLE DOMAINS

RELATED APPLICATIONS

Figure 1:
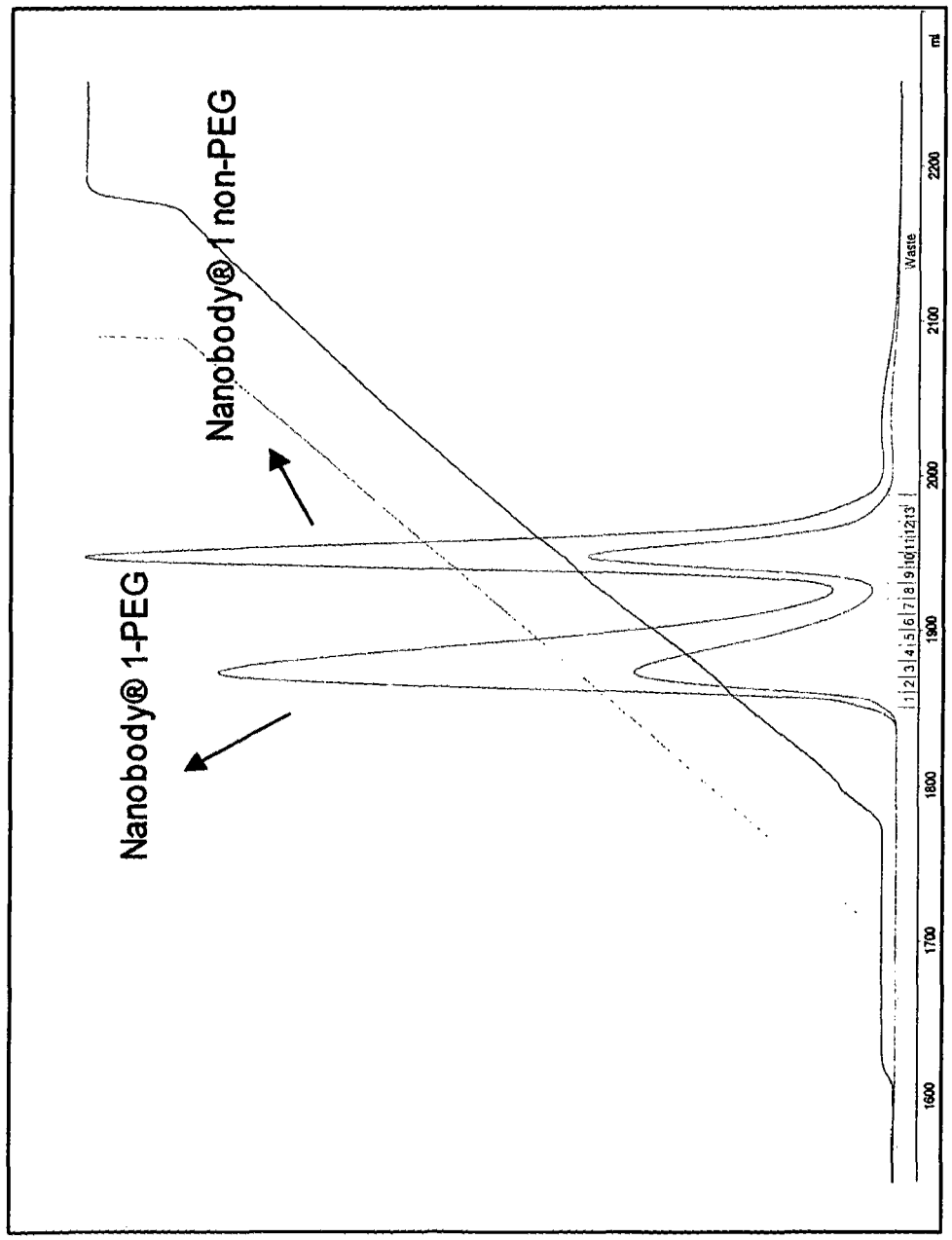

This application is a national stage filing under 35 U.S.C. §371 of international application PCT/EP2010/004196, filed Jul. 9, 2010, which claims the benefit under 35 U.S.C. §119(e) of U.S. provisional application Ser. No. 61/270,613, filed Jul. 10, 2009, the disclosures of which are incorporated by reference herein in their entireties.

FIELD OF THE INVENTION

The present invention relates to the expression and/or production of variable domains of immunoglobulins and/or antibodies. More particularly the present invention provides methods for the expression and/or production of variable domains with a C-terminal extension that can be used for coupling of the variable domain to one or more further groups, residues or moieties.

The present invention further provides variable domains (as defined herein) and polypeptides comprising one or more variable domains (also referred to as "polypeptides of the invention") obtainable by the methods of the present invention, as well as compounds (also referred to as "compounds of the invention") that comprise such variable domains and/or polypeptides coupled to one or more groups, residues or moieties.

The invention also relates to nucleic acids encoding such variable domains and/or polypeptides; to host cells comprising such nucleic acids and/or expressing or capable of expressing such variable domains and/or polypeptides; to compositions, and in particular to pharmaceutical compositions, that comprise such variable domains and/or polypeptides, compounds, nucleic acids and/or host cells; and to uses of such variable domains, polypeptides, nucleic acids, host cells and/or compositions, in particular for prophylactic, therapeutic or diagnostic purposes.

Other aspects, embodiments, advantages and applications of the invention will become clear from the further description herein.

BACKGROUND ART

Coupling of an antibody to one or more functional groups, residues or moieties may add one or more desired properties or functionalities to the antibody. Desired properties may include the possibility to attach the antibody to a solid phase, the introduction of a marker (such as e.g. an enzyme, biotin, gold particles, etc.), increase of the half-life, the solubility and/or the absorption of the antibody and/or attachment of a drug. Coupling of an antibody to one or more functional groups, residues or moieties may also reduce undesired properties such as reduction of the immunogenicity and/or the toxicity of the antibody. For a further description of possible modifications and/or groups, residues or moieties that might improve the properties of an antibody, references is also made to Remington's Pharmaceutical Sciences, 16th ed., Mack Publishing Co., Easton, Pa. (1980).

Chemical coupling of antibodies with drugs, radioisotopes, proteins or other molecules has been widely investigated (see e.g. Luttmann et al. Immunology, The Experimenter Series, Elsevier pp. 30-39; King D. J. Applications and Engineering of Monoclonal Antibodies, Taylor & Francis Books Ltd. ISBN: 0748404228, pp. 58-66; McCafferty et al. Antibody Engineering, A practical approach. Ed. Hames B. D., IRL Press) and a range of chemical approaches are available. Chemical conjugation is the only option for the attachment to antibodies of non-proteinaceous materials such as drugs and polyethylene glycol.

A variety of amino acid residues on the surface of the antibody molecule can be used for chemical modification and coupling such as tyrosine, aspartic and glutamic acid, lysine and cysteine. In the case of cysteine, antibody molecules do not normally contain a free thiol group as all of the available cysteine residues form disulphide bonds. In addition, loss of some or all of the antigen binding ability of the antibody is a common consequence of non-specific conjugation methods which may result from the modification of amino acids close to the antigen binding site. This is even more pronounced when antigen binding fragments are used. Therefore, functional groups are preferably attached to cysteines via a suitable linker or spacer. These linkers may provide an additional thiol group and might reduce the loss of functionality of the antibody due to sterical hindrance.

One of the most widely used techniques for increasing the half-life and/or reducing the immunogenicity of pharmaceutical proteins comprises attachment of a suitable pharmacologically acceptable polymer, such as polyethyleneglycol) (PEG) or derivatives thereof (such as methoxypoly(ethyleneglycol) or mPEG). The conjugation of the PEG to the target protein can be effected in a number of different ways (see e.g. Zalipsky 1995, Bioconjug. Chem. 6: 150-165; Greenwald et al. 2000, Crit. Rev. Ther. Drug Carrier Syst. 17: 101-161). Preferably, site-directed pegylation is used, in particular via a cysteine-residue (see for example Chapman et al. 1999, Nat. Biotechnol. 17: 780-783; Yang et al. 2003, Protein Eng. 16: 761-770). For example, PEG may be attached to a cysteine residue that naturally occurs in the protein, the protein may be modified so as to suitably introduce one or more cysteine residues for attachment of PEG, an amino acid sequence comprising one or more cysteine residues for attachment of PEG may be fused to the N- and/or C-terminus of the protein and/or one or more cysteine residues may be provided within a linker segment (Yang et al. 2003, Protein Eng. 16: 761-770; EP 1 160 255, WO 01/94585, EP 1 639 011).

Nanobodies (as further described herein) are characterized by formation of the antigen binding site by a single variable domain, which does not require interaction with a further domain (e.g. in the form of VH/VL interaction) for antigen recognition. Production of Nanobodies, in lower eukaryotic hosts such as *Pichia pastoris* has been extensively described in WO 94/25591. Attachment of functional groups, residues or moieties, such as polyethylene glycol, to a Nanobody has been described e.g. in WO 08/101985, WO 08/142164, WO 09/068625, WO 09/068627 and WO 08/020079.

SUMMARY OF THE INVENTION

The present invention is based on the surprising finding that expression in a host of one or more variable domains with a cysteine containing linker and subsequent pegylation showed only very low pegylation yields. The expression and/or production of the variable domains with the cysteine containing linker had resulted in a very low amount of variable domain that still contained the cysteine residue in the linker needed for attachment of the PEG molecule. Certain cysteine containing C-terminal extensions or linkers on the variable domain appeared susceptible to the carboxypeptidase activity of the host. The present invention provides methods for the expression and/or production of one or more variable domains, or single variable domains, which overcome this unexpected problem.

In one aspect, the present invention provides improved methods for the expression and/or production of variable domains, preferably single variable domains, with a cysteine containing linker, characterized in that a yield of at least 80% of variable domains with a cysteine containing C-terminal extension is obtained. More particularly, the present invention provides methods for the expression and/or production of a polypeptide (also referred to as "polypeptide of the invention") comprising one or more variable domains, preferably single variable domains, and a C-terminal extension of maximal 10 amino acid residues in which at least one amino acid residue is a cysteine residue, said methods comprising the steps of:

a) maintaining a host under conditions that are such that said host expresses and/or produces the polypeptide;
b) isolating and/or purifying the secreted polypeptide from the medium;

wherein at least 80% of the variable domain isolated and/or purified in step b) contains the at least one cysteine residue in the C-terminal extension, as determined by mass spectrometry.

Preferably, at least 90%, more preferably at least 95%, even more preferably at least 99% of the polypeptide isolated and/or purified in step b) contains the at least one cysteine residue in the C-terminal extension, as determined by mass spectrometry.

The present inventors surprisingly observed that the expression and/or production of one or more variable domains with a C-terminal extension consisting of SEQ ID NO: 1 gave a very low portion (80% or less) of the variable domains that could be pegylated (i.e. that still contained the cysteine residue). Accordingly, in another aspect, the present invention provides methods for the expression and/or production of one or more variable domains with a C-terminal extension that is different from SEQ ID NO: 1. More particularly, the present invention provides methods for the expression and/or production of a polypeptide comprising one or more variable domains, preferably single variable domains, with a C-terminal extension that is different from SEQ ID NO: 1, said methods comprising the steps of:

a) maintaining a host under conditions that are such that said host expresses and/or produces the polypeptide;
b) isolating and/or purifying the secreted polypeptide from the medium;
wherein at least 80% of the variable domain isolated and/or purified in step b) has the at least one cysteine residue in the C-terminal extension, as determined by mass spectrometry.

The at least one cysteine residue present in the C-terminal extension of the variable domain may or may not be positioned at the C-terminal end of the C-terminal extension. Accordingly, in one aspect of the invention, the polypeptide of the invention expressed and/or produced comprises at least one cysteine residue at the C-terminal end of the C-terminal extension. In this aspect of the invention, the C-terminal extension should be different from SEQ ID NO: 1. In another aspect of the invention, the polypeptide of the invention expressed and or produced comprises at least one cysteine residue at a site in the C-terminal extension different from the C-terminal end.

The C-terminal extension encompassed in the polypeptide of the invention may comprise and/or consist of different amino acid residues as long as these amino acid residues (and their order) provide the desired property (i.e. serve as a linker for the attachment of one or more functional groups, residues or moieties) to the C-terminal extension and as long as these amino acid residues (and their order) provide a yield of at least 80% (preferably 90%, more preferably 95%, most preferably 99%) of the variable domain with the cysteine containing C-terminal extension.

Accordingly, in a non-limiting aspect, in addition to the at least one cysteine residue, the C-terminal extension encompassed in the polypeptide of the invention comprises or essentially consists of glycine residues. In this aspect of the invention, the C-terminal extension should be different from SEQ ID NO: 1. The C-terminal extension should preferably also be different from a linker comprising three glycine residues followed by a C-terminal cysteine residue (i.e. comprising C-terminally following sequence: GGGC(SEQ ID NO: 1)). In another non-limiting aspect, in addition to the at least one cysteine residue, the C-terminal extension encompassed in the polypeptide of the invention comprises or essentially consists of alanine residues. In yet another non-limiting aspect, the C-terminal extension encompassed in the polypeptide of the invention comprises or essentially consists of an amino acid sequence selected from any of SEQ ID NO's: 2-7 or the C-terminal amino acid of the one or more single variable domains is removed prior to addition of a C-terminal cysteine (e.g., as shown in SEQ ID NO: 8).

The host used for the expression and or production of the polypeptide of the invention may be selected from prokaryotic hosts or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis,* preferably *Pichia pastoris*.

The one or more variable domains expressed and/or produced in the method of the present invention may be, without being limiting, a variable domain that is a light chain variable domain sequence or a heavy chain variable domain sequence, more specifically a variable domain which is a heavy chain variable domain sequence that is derived from a conventional four-chain antibody or a heavy chain variable domain sequence that is derived from a heavy chain antibody, in particular a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody (including but not limited to a VHH sequence), preferably a Nanobody.

In a further aspect of the invention, the polypeptide of the invention, comprising one or more variable domains and the cysteine containing C-terminal extension, is coupled to one or more groups, residues or moieties. Accordingly, the present invention also relates to a method for the expression and/or production of a compound comprising one ore more variable domains coupled via at least one cysteine residue present in a C-terminal extension of maximal 10 amino acid residues to one or more groups, residues or moieties, said method comprising the steps of:

a) maintaining a host under conditions that are such that said host expresses and/or produces a polypeptide comprising the one or more variable domains and the C-terminal extension;
b) isolating and/or purifying the secreted polypeptide from the medium wherein at least 80% of the polypeptide isolated and/or purified has the at least one cysteine residue in the C-terminal extension, as determined by mass spectrometry;

c) coupling one or more groups, residues or moieties to the at least one cysteine residue present in the C-terminal extension.

Preferably, at least 90%, more preferably at least 95%, even more preferably at least 99% of the polypeptide isolated and/or purified in step b) contains the at least one cysteine residue in the C-terminal extension, as determined by mass spectrometry.

Groups, residues or moieties that can be coupled to the at least one cysteine present in the C-terminal extension will be known to persons skilled in the art. Preferably these groups, residues or moieties provide one or more desired property and/or reduce one or more undesired properties to the variable domain. In one aspect, the one or more groups, residues or moieties are selected from polyethylene glycol (PEG), a peptide, a small molecule drug, a lipid, a radiolabelled molecule.

The present invention also relates to polypeptides (also referred to as "polypeptides of the invention") and compounds (also referred to as "compounds of the invention") obtainable and/or obtained by the methods of the present invention, to nucleic acids encoding the polypeptides of the invention, to host cells comprising such nucleic acids and/or expressing the polypeptides of the invention, to pharmaceutical compositions and other compositions comprising such polypeptides, compounds or nucleic acids, and to diagnostic, prophylactic and/or therapeutic uses of the polypeptides, the compounds or compositions comprising the same, or methods of diagnosis, prevention and/or treatment comprising the use of the polypeptides, compounds or compositions comprising the same.

FIGURE LEGENDS

FIG. 1: PEGylated Nanobody 1-GGGC (SEQ ID NO: 10) was separated from respectively the free non-reacted PEG and the non-PEGylated Nanobody via CEX using a Macro-Cap SP chromatography step, during respectively the flow through fraction and the NaCl-gradient elution.

Figure 2:
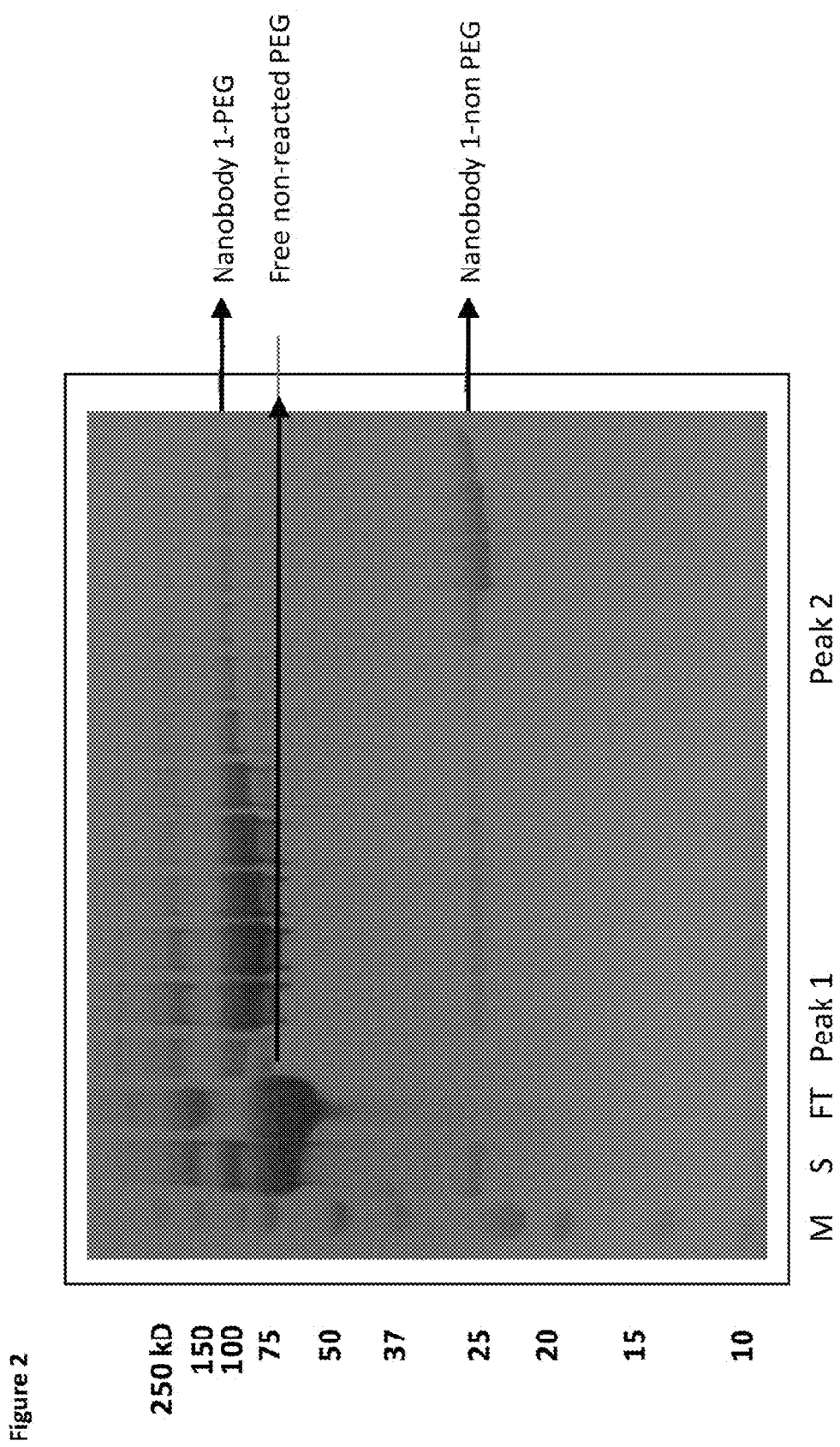

FIG. 2: LDS-page analysis of each fraction of the Macro-Cap SP chromatography step (as described in Example 1) after Coomassie brilliant blue staining followed by a PEG-staining. After the Coomassie brilliant blue staining the gel was destained in Milli-Q water followed by incubation for 5 minutes, with a mix of 10 ml 5% Barium chloride+4 ml 0.1M Iodine solution. Background was washed away using Milli-Q water.

Figure 3:
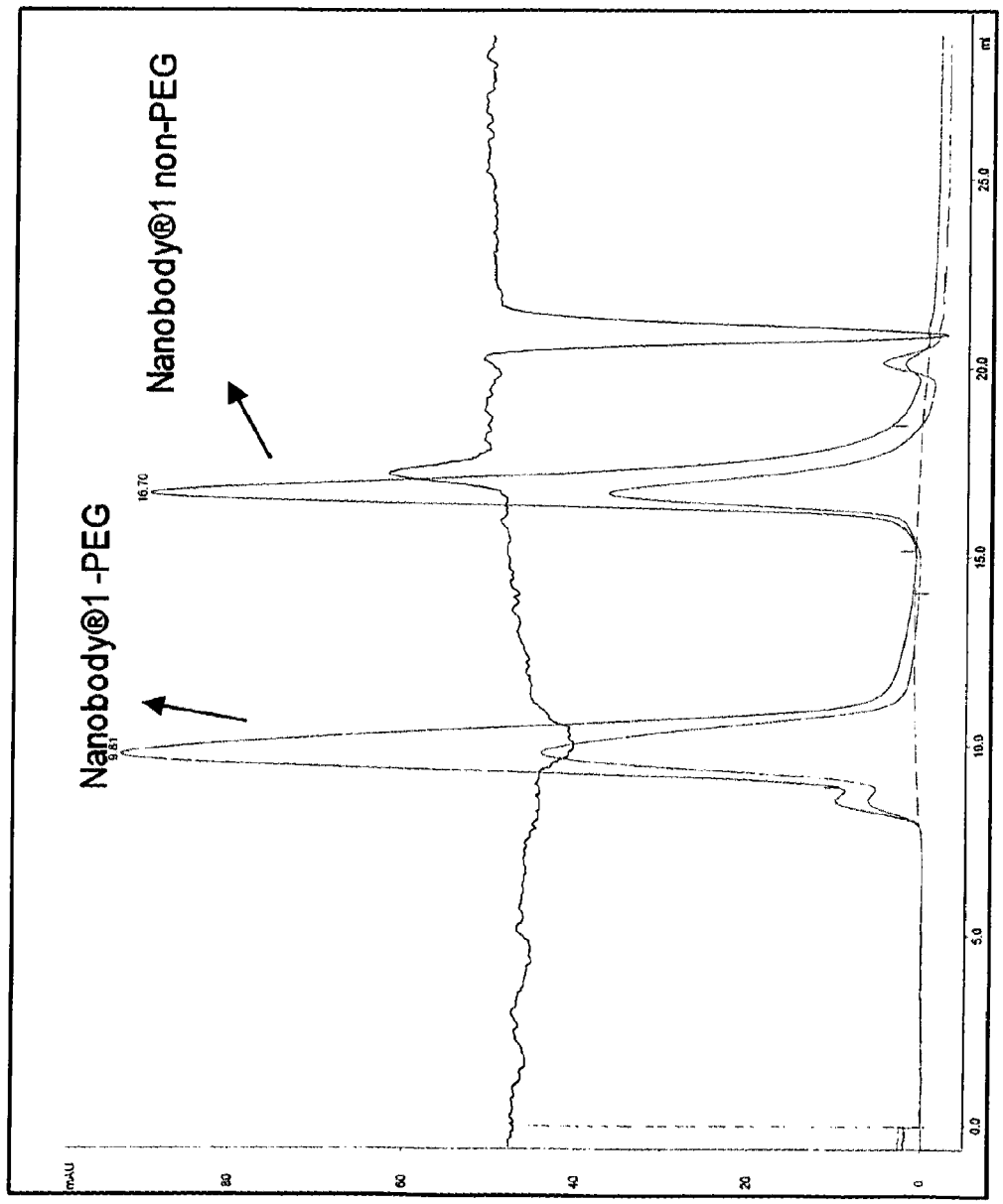

FIG. 3: Analytical Size exclusion chromatography analysis of the PEGylated Nanobody 1 before the removal of the non-reacted Nanobody 1 and free PEG40 as described in Example 1.

FIG. 4: (a) Immunoblot analysis of the biotinylated (lane 1) and mAlanine (lane 3) coupled Nanobody 1 after LDS-page using anti-VHH antiserum (1/1000 diluted in blocking buffer PBS, 1% casein); (b) Coomassie brilliant blue staining after LDS-page analysis of PEGylated (lane 1) biotinylated (lane 3) and mAlanine (lane 4) coupled Nanobody 1.

Figure 5:
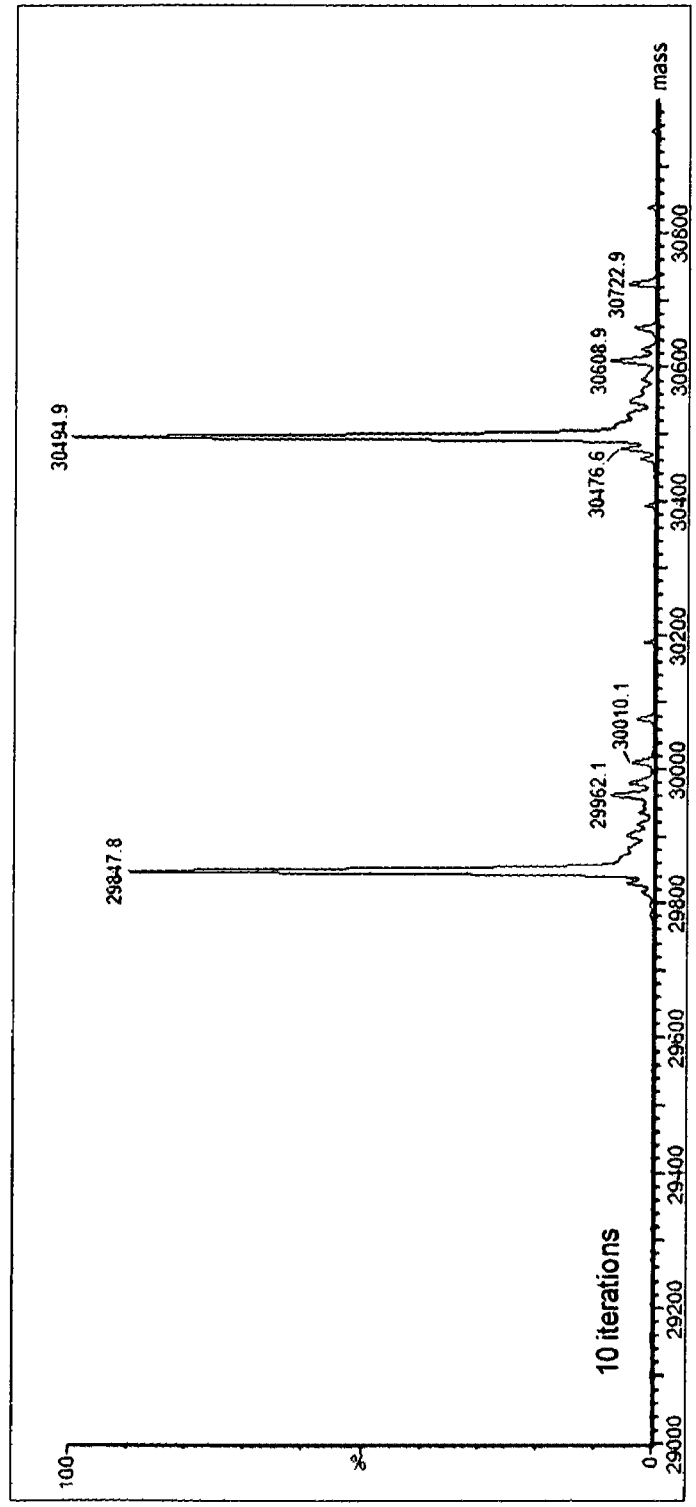

FIG. 5: Narrow range high resolution (10 iterations) MaxEnt1 deconvolution of the raw mass spectrum of the peak seen in the LC-MS profile of Nanobody 1_mBiotinylated.

Figure 6:
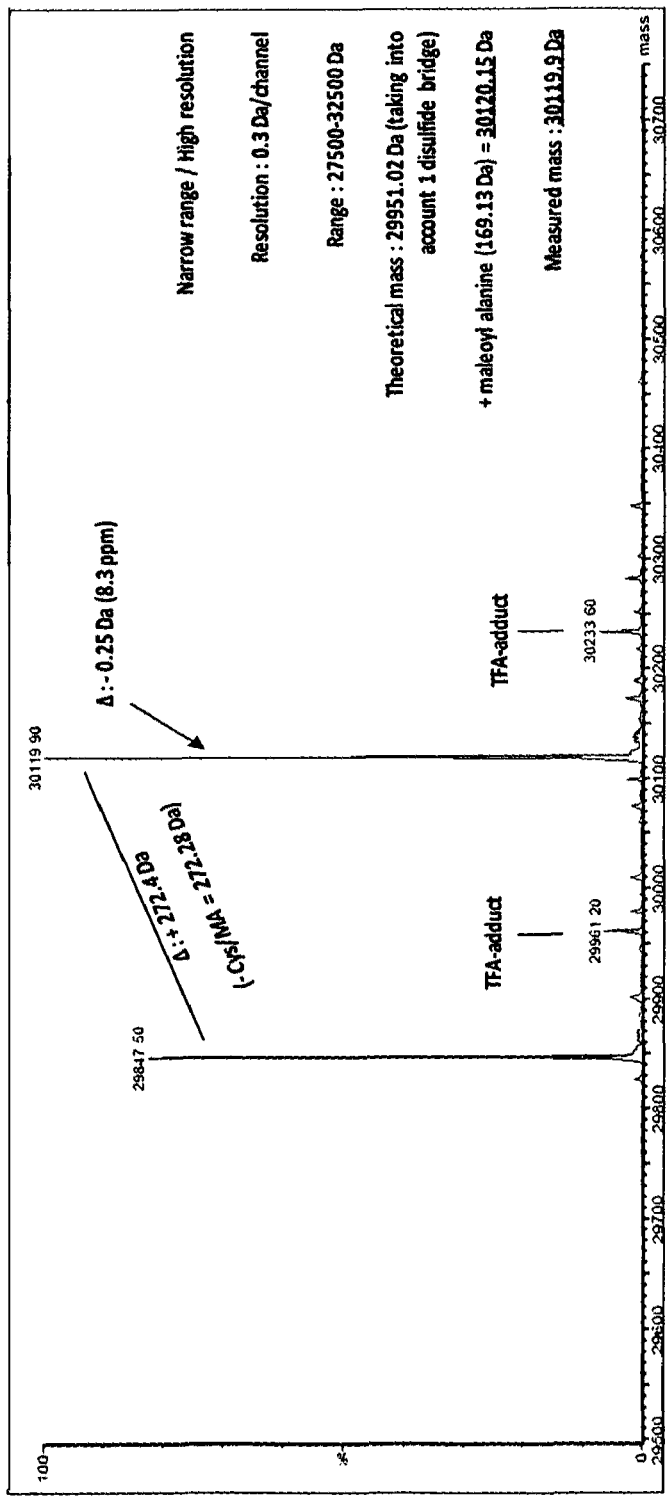

FIG. 6: Narrow range high resolution iteration to convergence. MaxEnt1 deconvolution of the raw mass spectrum of the peak seen in the LC-MS profile of Nanobody 1_mAlanine coupled.

Figure 7:
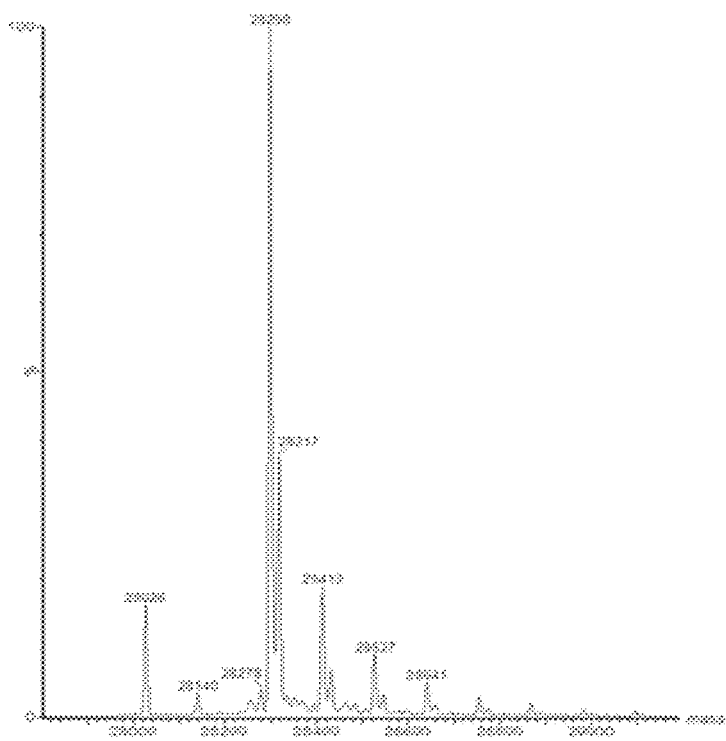

FIG. 7: LC/MS analysis of Nanobody 2-GGGC-Alanine (Nanobody 2-GGGC is SEQ ID NO: 19) as described in Example 3. Approximately 20% of the material had no C-terminal cysteine.

Figure 8:
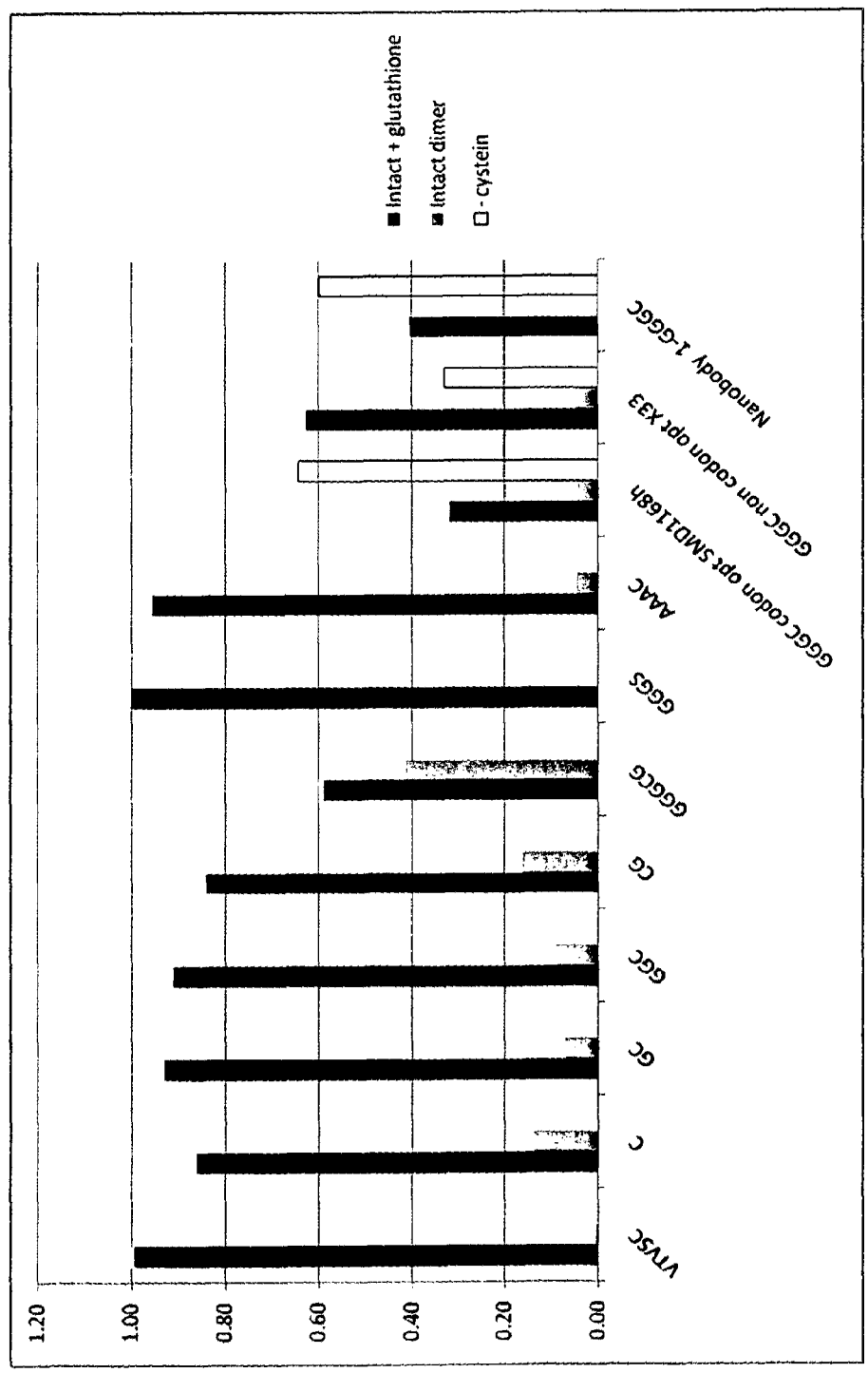

FIG. 8: Relative peak height of intact protein (monomer and dimer), and C-terminal cysteine truncated protein, as detected by LC-MS for constructs with different linker lengths as described in Example 4.

Figure 9:
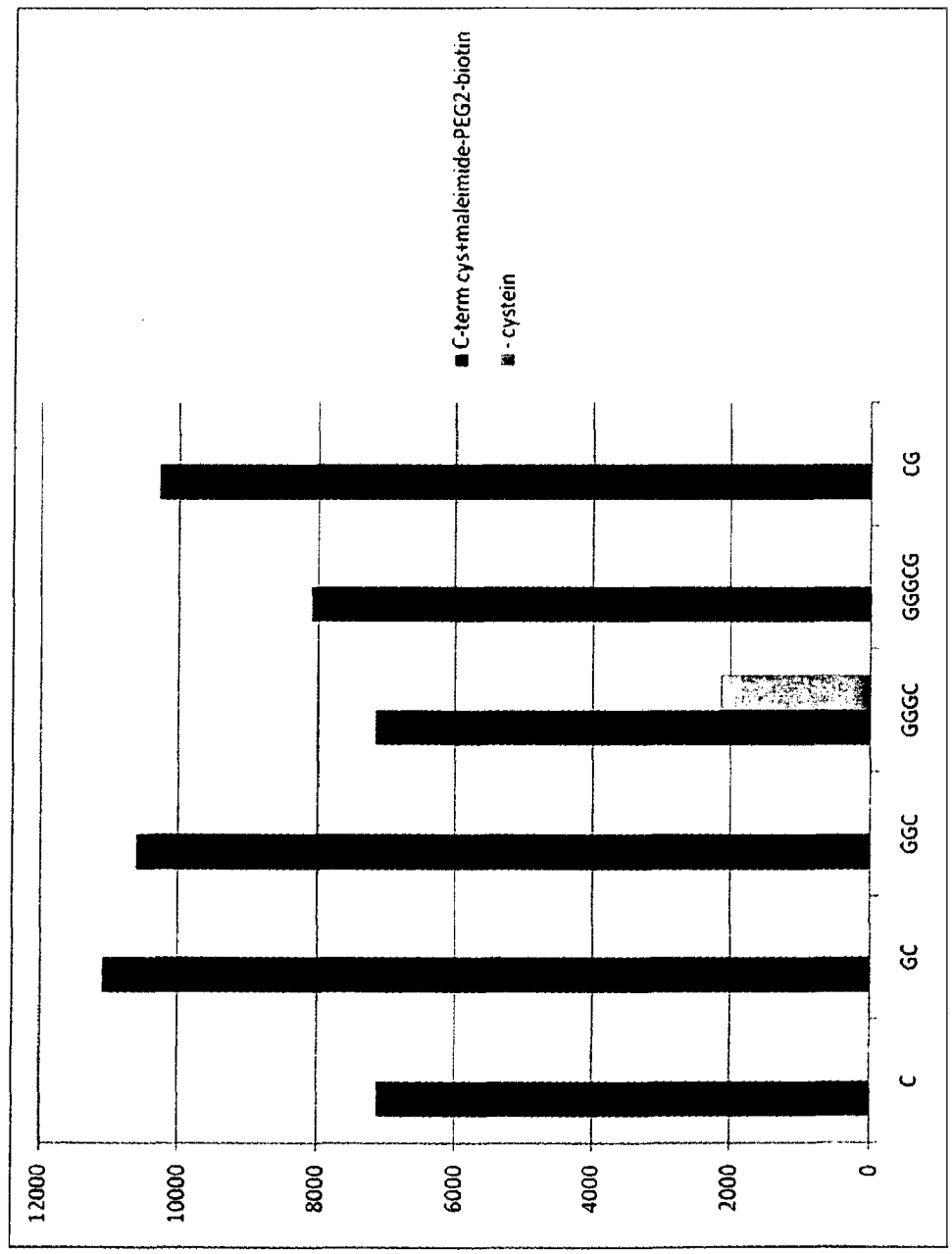

FIG. 9: Peak height measured by LC-MS (purity and identity analysis) of protein coupled to maleimide-PEG2-biotin (mimic of pegylation reaction). Only in the construct with the three-glycine linker, not all protein was free for the pegylation reaction because C-terminal cysteine-truncated protein had occurred.

DETAILED DESCRIPTION

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, New York (2005), as well as to the general background art cited herein.

The term "variable domain" (or "immunoglobulin variable domain") refers to the part or domain of an immunoglobulin molecule or antibody which is partially or fully responsible for antigen binding. The term "single variable domain" (or "immunoglobulin single variable domain"), defines molecules wherein the antigen binding site is present on, and formed by, a single immunoglobulin domain. This sets single variable domains apart from "conventional" immunoglobulins or their fragments, wherein two immunoglobulin domains, in particular two "variable domains" interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of a single variable domain is formed by a single VH or VL domain. Hence, the antigen binding site of a single variable domain is formed by no more than three CDRs. The term "single variable domain" does comprise fragments of conventional immunoglobulins wherein the antigen binding site is formed by a single variable domain.

Generally, single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

In one aspect of the invention, the single variable domains are light chain variable domain sequences (e.g. a $V_L$-sequence), or heavy chain variable domain sequences (e.g. a $V_H$-sequence); more specifically, the single variable domains can be heavy chain variable domain sequences that are derived from a conventional four-chain antibody or heavy chain variable domain sequences that are derived from a heavy chain antibody.

The single variable domain may be a domain antibody (or an amino acid sequence that is suitable for use as a domain antibody), a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$ sequence) [Note: Nanobody® and Nanobodies® are registered trademarks of Ablynx N.V.]; other single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341 (6242): 544-546), to Holt et al. 2003 (Trends Biotechnol. 21(11): 484-490); as well as to for example WO 04/068820, WO 06/030220, WO 06/003388 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629).

In particular, the amino acid sequence of the invention may be a Nanobody or a suitable fragment thereof. For a further description of $V_{HH}$'s and Nanobodies, reference is made to the review article by Muyldermans 2001 (Reviews in Molecular Biotechnology 74: 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular $V_{HH}$ sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

Thus, in the meaning of the present invention, the term "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as previously described.

The term "single variable domain" also encompasses variable domains of different origin, comprising mouse, rat, rabbit, donkey, human and camelid variable domains; as well as fully human, humanized or chimeric variable domains. For example, the invention comprises camelid variable domains and humanized camelid variable domains, or camelized variable domains, e.g. camelized dAb as described by Ward et al (see for example WO 94/04678 and Davies and Riechmann (1994, FEBS Lett. 339(3): 285-290) and (1996, Protein Eng. 9(6): 531-537)). Moreover, the invention comprises fused variable domains, e.g. forming a multivalent and/or multispecific construct (for multivalent and multispecific polypeptides containing one or more $V_{HH}$ domains and their preparation, reference is also made to Conrath et al. 2001 (J. Biol. Chem. 276: 7346-7350) as well as to for example WO 96/34103 and WO 99/23221).

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies.

The single variable domains provided by the invention are preferably in essentially isolated form (as defined herein), or form part of a polypeptide of the invention (as defined herein), which may comprise or essentially consist of one or more single variable domains and which may optionally further comprise one or more further amino acid sequences (all optionally linked via one or more suitable linkers). For example, and without limitation, the one or more single variable domains may be used as a binding unit in such a polypeptide, which may optionally contain one or more further amino acid sequences that can serve as a binding unit (i.e. against one or more other targets), so as to provide a monovalent, multivalent or multispecific polypeptide of the invention, respectively as e.g. described in WO 08/101985, WO 08/142164, WO 09/068625, WO 09/068627 and WO 08/020079. Such a protein or polypeptide may also be in essentially isolated form (as defined herein) and the methods of the present invention for the expression and/or production of single variable domains equally apply to polypeptides comprising one or more single variable domains.

According to the invention, the term "single variable domain" may comprise constructs comprising two or more antigen binding units in the form of single variable domain, as outlined above. For example, two (or more) variable domains with the same or different antigen specificity can be linked to form e.g. a bivalent, trivalent or multivalent construct. By combining variable domains of two or more specificities, bispecific, trispecific etc. constructs can be formed. For example, a variable domain according to the invention may comprise two variable domains directed against target A, and one variable domain against target B. Such constructs and modifications thereof, which the skilled person can readily envisage, are all encompassed by the term variable domain as used herein. In the method of the present invention these molecules will also encompass a C-terminal extension and are also referred to as "polypeptide of the invention" or "polypeptides of the invention".

"Polypeptide of the invention" or "polypeptides of the invention" thus refers to a polypeptide comprising one or more (single) variable domains attached to a C-terminal extension or C-terminal linker of maximal 10 amino acid residues in which at least one amino acid residue is a cysteine residue. Accordingly, a "polypeptide of the invention" may be a polypeptide comprising a (single) variable domain attached to a C-terminal extension or C-terminal linker of maximal 10 amino acid residues in which at least one amino acid residue is a cysteine residue; and a "polypeptide of the invention" may be a polypeptide comprising two or more (single) variable domains attached to a C-terminal extension or C-terminal linker of maximal 10 amino acid residues in which at least one amino acid residue is a cysteine residue.

The terms "C-terminal extension" or "C-terminal linker" are used interchangeable herein and refer to an amino acid spacer or linker that is present at the C-terminal end of the variable domain and/or polypeptide of the invention. This amino acid spacer or linker is usually present C-terminally of the last amino acid residue (usually a serine residue) of the variable domain. However, this amino acid spacer or linker may also be present C-terminally of the second last amino acid residue (usually a serine residue) or third last (usually a valine residue) amino acid residue of the variable domain. If this is the case, the last amino acid residue or the last and second last amino acid residues respectively of the variable domain are absent.

In the context of the present invention, the C-terminal extension may consist of at least one amino acid residue to maximal 10 amino acid residues, preferably between 2 and 8 amino acid residues, such as 2, 3, 4, 5, 6, 7 or 8 amino acid residues.

It has surprisingly been observed that expression and/or production of variable domains with a C-terminal extension that consists of SEQ ID NO: 1 gave variable domain yields wherein only a small portion (lower than 80%) of the variable domain still contained the cysteine residue. Therefore, the C-terminal extension encompassed in the polypeptide of the invention should preferably not consist of SEQ ID NO: 1. The C-terminal extension encompassed in the polypeptide of the invention should preferably also not comprise three glycine residues followed by a C-terminal cysteine residue (i.e. comprise C-terminally the sequence GGGC (SEQ ID NO: 1)).

The terms "cysteine containing C-terminal extension" or "cysteine containing C-terminal linker" are used interchangeable and refer to a C-terminal extension that comprises at least one cysteine residue.

In one aspect of the invention, the at least one cysteine residue is present or positioned at the C-terminal end of the C-terminal extension. For example, the C-terminal extension may consist of 1, 2, 3, 5, 6, 7 or 8 amino acid residues of which the C-terminal amino acid residue is a cysteine residue; such as e.g. the C-terminal extension may consist of only a cysteine residue; the C-terminal extension may consist of 1, 2, 4, 5, 6 or 7 amino acid residues followed by a cysteine residue; the C-terminal extension may consist of 1, 2, 4, 5, 6 or 7 glycine residues followed by a cysteine residue; the C-terminal extension may consist of 1, 2, 3, 4, 5, 6 or 7 alanine residues followed by a cysteine residue.

In another aspect, the cysteine residue is present or positioned at a site in the C-terminal extension which is different from the C-terminal end, such as, for example, at the amino acid residue in front of (upstream of) the last amino acid residue of the C-terminal extension (i.e. the second last amino acid residue of the polypeptide of the invention) or at the amino acid residue in front of (upstream of) the last two amino acid residue of the C-terminal extension (i.e. the third last amino acid residue of the polypeptide of the invention). For example, the C-terminal extension may consist of 2, 3, 4, 5, 6, 7 or 8 amino acid residues (such as e.g. glycine or alanine) of which respectively the first, second, third, fourth, fifth, sixth or seventh amino acid residue is a cysteine (i.e. the second last amino acid residue of the polypeptide of the invention); or the C-terminal extension may consist of 3, 4, 5, 6, 7 or 8 amino acid residues (such as e.g. glycine or alanine) of which respectively the first, second, third, fourth, fifth or sixth amino acid residue is a cysteine (i.e. the third last amino acid residue of the polypeptide of the invention).

Examples of C-terminal extensions are given in Table 1.

The presence of the cysteine residue in the C-terminal extension in the polypeptide of the invention and the percentage of polypeptides that still contain a cysteine residue in the C-terminal extension can be determined by any method know in the art for the determination of the presence of amino acid residues, including but not limited to Liquid Chromatography such as Reverse Phase Chromatography or Ion Exchange Chromatography, and/or Mass spectrometry.

The terms "host" and "host cells" are used interchangeably. In the method of the present invention any host can be used without limitation, provided that they are suitable for the production of variable domains. In particular, the present invention relates to the use of hosts wherein expression of a variable domain with a C-terminal extension that consists of SEQ ID NO: 1 results in variable domain yields wherein only a small portion (lower than 80%) of the variable domain still contains the cysteine residue.

Specific examples of suitable hosts comprise prokaryotic organisms, such as coryneform bacteria or enterobacteriaceae. Also comprised are insect cells, in particular insect cells suitable for baculovirus mediated recombinant expression like *Trichoplusia* or *Spodoptera frugiperda* derived cells, including, but not limited to BTI-TN-5B1-4 High Five™ insect cells (Invitrogen), SF9 or Sf21 cells; mammalian cells like CHO cells and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporid-*

*iobolus, Endomycopsis*. Yeast is a preferable host of the present invention, and particularly preferred is *P. pastoris*.

In one aspect, the present invention relates to the use of non-*E. coli* hosts. In particular, the present invention relates to the use of non-*E. coli* hosts wherein expression of a variable domain with a C-terminal extension that consists of SEQ ID NO: 1 results in variable domain yields wherein only a small portion (lower than 80%) of the variable domain still contains the cysteine residue. Accordingly, the host used for the expression and or production of the polypeptide of the invention may be selected from prokaryotic hosts other than *E. coli* or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, preferably *Pichia pastoris*.

The host used in the method of the present invention will be capable of producing the polypeptide of the invention. It will typically be genetically modified to comprise one or more nucleic acid sequences encoding the polypeptide of the invention. Non-limiting examples of genetic modifications comprise the transformation e.g. with a plasmid or vector, or the transduction with a viral vector. Some hosts can be genetically modified by fusion techniques. Genetic modifications include the introduction of separate nucleic acid molecules into a host, e.g. plasmids or vectors, as well as direct modifications of the genetic material of the host, e.g. by integration into a chromosome of the host, e.g. by homologous recombination. Oftentimes a combination of both will occur, e.g. a host is transformed with a plasmid, which, upon homologous recombination will (at least partly) integrate into the host chromosome. The skilled person knows suitable methods of genetic modification of the host to enable the host to produce variable domains.

General methods for producing variable domains and/or polypeptides in different hosts are known to the skilled person and/or have been described in the art. For example, production of Nanobodies in lower eukaryotic hosts such as *Pichia pastoris* has been extensively described in WO 94/25591. The contents of this application are explicitly referred to in the connection with general culturing techniques and methods, including suitable media and conditions. The contents of this document are incorporated by reference. The skilled person can also devise suitable genetic constructs for expression of the polypeptides of the invention in different hosts on the basis of the present application and common general knowledge. The present invention also relates to conditions and genetic constructs described in the art, for example the general culturing methods, plasmids, promoters and leader sequences described in WO 94/25591, WO 08/020079, Gasser et al. 2006 (Biotechnol. Bioeng. 94: 535); Gasser et al. 2007 (Appl. Environ. Microbiol. 73: 6499); or Damasceno et al. 2007 (Microbiol. Biotechnol. 74: 381).

More particularly, the present invention provides a method for the expression and/or production of a polypeptide comprising one or more single variable domains and comprising a C-terminal extension of maximal 10 amino residues in which at least one amino acid residue is a cysteine residue, said method at least comprising the steps of:
 a) cultivating a host or host cell (as defined herein) under conditions that are such that said host or host cell will multiply;
 b) maintaining said host or host cell under conditions that are such that said host or host cell expresses and/or produces the polypeptide;
 c) isolating and/or purifying the secreted polypeptide from the medium,
wherein at least 80% of the polypeptide isolated and/or purified in step c) contains the at least one cysteine residue in the C-terminal extension, as determined by mass spectrometry.

To produce/obtain expression of the polypeptide, the transformed host cell or transformed host organism may generally be kept, maintained and/or cultured under conditions such that the (desired) polypeptide is expressed/produced. Suitable conditions will be clear to the skilled person and will usually depend upon the host cell/host organism used, as well as on the regulatory elements that control the expression of the (relevant) nucleotide sequence. Again, reference is made to the handbooks and patent applications mentioned above.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

In a specific aspect, the host organism is kept, maintained and/or cultured under conditions that reduce the activity of the carboxypeptidase enzyme, and/or that reduce the conversion of the inactive form of the carboxypeptidase to its active form (e.g. by inhibition of the enteropeptidases). Without being limiting, such conditions may include lowering the pH during culturing, shortening the culturing time and/or the addition of metal chelators.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the polypeptide to be isolated).

In the present invention, the host can be removed from the culture medium by routine means. For example, the host can be removed by centrifugation or filtration. The solution obtained by removal of the host from the culture medium is also referred to as culture supernatant, or clarified culture supernatant. The polypeptides of the invention can be purified from the culture supernatant by standard methods. Standard methods include, but are not limited to chromatographic methods, including size exclusion chromatography, hydrophobic chromatography, ion exchange chromatography, and affinity chromatography. These methods can be performed alone or in combination with other purification methods, e.g. precipitation or gel electrophoresis. The skilled person can devise suitable combinations of purification methods for the polypeptides of the invention on the basis of common general knowledge. For specific examples the art cited herein is referred to.

In one exemplary embodiment, the polypeptides of the invention can be purified from culture supernatant by a combination of affinity chromatography on Protein A, ion exchange chromatography and size exclusion chromatography. Reference to any "step of purification", includes, but is not limited to these particular methods.

More specifically, the polypeptides of the invention can be purified from culture supernatant using a process wherein the clarified supernatant (e.g. obtained by centrifugation) is captured on an affinity chromatography resin such as Protein A resin; followed by a polish step, which can comprise an CIEX or an AIEX step using for example Poros 50HS (POROS), SOURCE 30S or SOURCE 15S (GE Healthcare), SP Sepharose (GE healthcare), Capto S (GE healthcare) or Poros 50HQ (POROS), SOURCE 30Q or SOURCE 15Q (GE Healthcare), Q Sepharose (GE healthcare), Capto Q and DEAE Sepharose (GE healthcare), followed by a second polish step such as a Size exclusion chromatography step using for example Superdex 75 or Superdex 200 (GE Healthcare) followed by a final formulation step using TFF (UF/DF).

In a further aspect, the invention also relates to a method as described above comprising the further step of coupling or attaching one or more groups, residues or moieties to the at least one cysteine residue present in the C-terminal extension. Accordingly, the present invention relates to a method comprising the steps of:
  a) maintaining a host under conditions that are such that said host expresses and/or produces a polypeptide comprising one or more variable domains and a C-terminal extension of maximal 10 amino acid residues in which at least one amino acid residue is a cysteine residue;
  b) isolating and/or purifying the secreted polypeptide from the medium wherein at least 80% (preferably at least 90%, more preferably at least 95%, most preferably at least 99%) of the polypeptide isolated and/or purified contains the at least one cysteine residue in the C-terminal extension, as determined by mass spectrometry;
  c) coupling one or more groups, residues or moieties to the at least one cysteine residue present in the C-terminal extension.

Examples of such groups, residues or moieties and methods and techniques that can be used to attach such groups, residues or moieties and the potential uses and advantages of such groups, residues or moieties will be clear to the skilled person. Without being limiting, thiol reactive groups for antibody modification include maleimide, vinylsulphone, haloacetyl or pyridyl disulphide groups. Maleimides react selectively with cysteines at neutral pH, although there is reactivity with amine groups at higher pH values. A stable thioether bond is generated.

One or more functional groups, residues or moieties may be attached to the polypeptide of the invention that confer one or more desired properties or functionalities to the polypeptide of the invention. Example of such functional groups, residues or moieties will be clear to the skilled person. For example, such one or more functional groups, residues or moieties may increase the half-life, the solubility and/or the absorption of the polypeptide of the invention, such one or more functional groups, residues or moieties may reduce the immunogenicity and/or the toxicity of the polypeptide of the invention, such one or more functional groups, residues or moieties may eliminate or attenuate any undesirable side effects of the polypeptide of the invention, and/or such one or more functional groups, residues or moieties may confer other advantageous properties to and/or reduce the undesired properties of the polypeptide of the invention; or any combination of two or more of the foregoing. Examples of such functional groups, residues or moieties and of techniques for introducing them will be clear to the skilled person, and can generally comprise all functional groups, residues or moieties and techniques mentioned in the general background art cited hereinabove as well as the functional groups, residues or moieties and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980).

One or more detectable labels or other signal-generating groups, residues or moieties may be coupled to the polypeptide of the invention, depending on the intended use of the labelled polypeptide. Suitable labels and techniques for attaching, using and detecting them will be clear to the skilled person, and for example include, but are not limited to, the fluorescent labels, phosphorescent labels, chemiluminescent labels, bioluminescent labels, radio-isotopes, metals, metal chelates, metallic cations, chromophores and enzymes, such as those mentioned on page 109 of WO 08/020079. Other suitable labels will be clear to the skilled person, and for example include moieties that can be detected using NMR or ESR spectroscopy.

Such labelled polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

A functional group, residue or moiety may be attached that is one part of a specific binding pair, such as the biotin-(strept) avidin binding pair. Such a functional group may be used to link the polypeptide of the invention to another protein, polypeptide or chemical compound that is bound to the other half of the binding pair, i.e. through formation of the binding pair. For example, a polypeptide of the invention may be conjugated to biotin, and linked to another protein, polypeptide, compound or carrier conjugated to avidin or streptavidin. For example, such a conjugated polypeptide may be used as a reporter, for example in a diagnostic system where a detectable signal-producing agent is conjugated to avidin or streptavidin. Such binding pairs may for example also be used to bind the polypeptide of the invention to a carrier, including carriers suitable for pharmaceutical purposes. One non-limiting example are the liposomal formulations described by Cao and Suresh 2000 (Journal of Drug Targeting 8 (4): 257). Such binding pairs may also be used to link a therapeutically active agent to the polypeptide of the invention.

For some applications, in particular for those applications in which it is intended to kill a cell that expresses the target against which the polypeptide of the invention is directed (e.g. in the treatment of cancer), or to reduce or slow the growth and/or proliferation such a cell, the polypeptide of the invention may also be linked to a toxin or to a toxic residue or moiety. Examples of toxic moieties, compounds or residues which can be linked to a Nanobody of the invention to provide—for example—a cytotoxic compound will be clear to the skilled person and can for example be found in the prior art cited above and/or in the further description herein.

Other potential chemical and enzymatical modifications will be clear to the skilled person. Such modifications may also be introduced for research purposes (e.g. to study function-activity relationships). Reference is for example made to Lundblad and Bradshaw 1997 (Biotechnol. Appl. Biochem. 26: 143-151).

One of the most widely used techniques for increasing the half-life and/or reducing the immunogenicity of pharmaceutical proteins comprises attachment of a suitable pharmacologically acceptable polymer, such as polyethyleneglycol)

(PEG) or derivatives thereof (such as methoxypoly(ethyleneglycol) or mPEG). Pegylation means the covalent attachment of polyethylene glycol (PEG) polymers to compounds. Pegylation of proteins and in particular antibodies has been described extensively (see e.g. Veronese 2001 (Biomaterials 22: 405-417); Bailon et al. 2001 (Bioconjug. Chem. 12: 195-202); Chapman 2002 (Adv. Drug Deliv. Rev. 54: 531-545); Veronese and Harris 2002 (Adv. Drug Deliv. Rev. 54: 453-456); Harris and Chess 2003 (Nat. Rev. Drug. Discov. 2: 214-221); Greenwald et al. 2003 (Bioconjug. Chem. 14: 395-403); WO 04/060965).

Generally, any suitable form of pegylation can be used, such as the pegylation used in the art for antibodies and antibody fragments (including but not limited to (single) domain antibodies and ScFv's); reference is made to for example Chapman 2002 (Adv. Drug Deliv. Rev. 54: 531-545); by Veronese and Harris 2002 (Adv. Drug Deliv. Rev. 54: 453-456), by Harris and Chess 2003 (Nat. Rev. Drug. Discov. 2: 214-221) and in WO 04/060965. Various reagents for pegylation of proteins are also commercially available, for example from Nektar Therapeutics (USA) or NOF Corporation (Japan).

Thiol-reactive PEGs include succinimidyl esters, p-nitrophenol carbonates, vinyl sulfone, tresylates, amino-, aminooxy-, tosyl-, methoxy- as well as maleimide-PEG (MAL-PEG) polymers (as e.g. described in Yang et al. 2003 (Protein Eng. 16: 761-770)). On top of this diversity, the size of the polymer can be chosen, typically form the range of 1000 Da up to 40-50 kDa, as well as the backbone structure (linear, branched or multiply branched star or comb-shaped molecules), as well as any kind of activated polyalkylene glycols including PPG (polypropylene glycol), PBG polybutylene glycol and PPG-PEG. The choice of the PEG molecule to be used for a particular application is made following consideration of a number of factors, such as the retention of an acceptable level of relevant biological activity or activities and the effect on the circulating half-life from the addition of the polymer.

Preferably, for polypeptides of the invention, a PEG is used with a molecular weight of more than 5000, such as more than 10,000 and less than 200,000, such as less than 100,000; for example in the range of 20,000-80,000.

The present invention also relates to a polypeptide obtainable by or obtained by the methods of the invention as described herein. More in particular, the present invention relates to a polypeptide comprising one or more variable domains, preferably single variable domains, and a C-terminal extension of maximal 10 amino acid residues in which at least one amino acid residue is a cysteine residue, said polypeptide obtainable by or obtained by:
  a) maintaining a host under conditions that are such that said host expresses and/or produces the polypeptide;
  b) isolating and/or purifying the secreted polypeptide from the medium;
wherein at least 80% (preferably at least 90%, more preferably at least 95%, most preferably at least 99%) of the polypeptide isolated and/or purified in step b) contains the at least one cysteine residue in the C-terminal extension, as determined by mass spectrometry.

In one aspect, the present invention relates to a polypeptide obtainable by or obtained by the methods of the invention as described herein and comprising one or more variable domains, preferably single variable domains, and a C-terminal extension of maximal 10 amino acid residues in which at least one amino acid residue is a cysteine residue, wherein the at least one cysteine residue is positioned at the C-terminal end of the C-terminal extension.

In another aspect, the present invention relates to a polypeptide obtainable by or obtained by the methods of the invention as described herein and comprising one or more variable domains, preferably single variable domains, and a C-terminal extension of maximal 10 amino acid residues in which at least one amino acid residue is a cysteine residue, wherein the at least one cysteine residue is positioned at a site in the C-terminal extension different from the C-terminal end.

In yet another aspect, the present invention relates to a polypeptide obtainable by or obtained by the methods of the invention as described herein and comprising one or more variable domains, preferably single variable domains, and a C-terminal extension of maximal 10 amino acid residues in which at least one amino acid residue is a cysteine residue, and which is different from SEQ ID NO: 1 and/or from a C-terminal extension comprising three glycine residues followed by a C-terminal cysteine residue (i.e. comprising C-terminally GGGC (SEQ ID NO: 1)). In one preferred aspect, the C-terminal extension, in addition to the at least one cysteine residue, consists of glycine and/or alanine residues. In another preferred aspect, the C-terminal extension is selected from SEQ ID NO's: 2-8.

In yet another aspect, the present invention relates to a polypeptide obtainable by or obtained by the methods of the invention as described herein and comprising one or more variable domains, preferably single variable domains, and a C-terminal extension of maximal 10 amino acid residues in which at least one cysteine residue is present or positioned at the C-terminal end of the C-terminal extension. For example, the C-terminal extension may consist of 1, 2, 3, 5, 6, 7 or 8 amino acid residues of which the C-terminal amino acid residue is a cysteine residue; such as e.g. the C-terminal extension may consist of only a cysteine residue; the C-terminal extension may consist of 1, 2, 4, 5, 6 or 7 amino acid residues followed by a cysteine residue; the C-terminal extension may consist of 1, 2, 4, 5, 6 or 7 glycine residues followed by a cysteine residue; the C-terminal extension may consist of 1, 2, 3, 4, 5, 6 or 7 alanine residues followed by a cysteine residue.

In yet another aspect, the present invention relates to a polypeptide obtainable by or obtained by the methods of the invention as described herein and comprising one or more variable domains, preferably single variable domains, and a C-terminal extension of maximal 10 amino acid residues in which the cysteine residue is present or positioned at a site in the C-terminal extension which is different from the C-terminal end, such as, for example, at the amino acid residue in front of (upstream of) the last amino acid residue of the C-terminal extension (i.e. the second last amino acid residue of the polypeptide of the invention) or at the amino acid residue in front of (upstream of) the last two amino acid residue of the C-terminal extension (i.e. the third last amino acid residue of the polypeptide of the invention). For example, the C-terminal extension may consist of 2, 3, 4, 5, 6, 7 or 8 amino acid residues (such as e.g. glycine or alanine) of which respectively the first, second, third, fourth, fifth, sixth or seventh amino acid residue is a cysteine (i.e. the second last amino acid residue of the polypeptide of the invention); or the C-terminal extension may consist of 3, 4, 5, 6, 7 or 8 amino acid residues (such as e.g. glycine or alanine) of which respectively the first, second, third, fourth, fifth or sixth amino acid residue is a cysteine (i.e. the third last amino acid residue of the polypeptide of the invention).

The polypeptide of the invention is characterized by a reduced level (less than 20%, preferably less than 10%, more preferably less than 5%, most preferably less than 1%), or the complete absence, of polypeptide lacking the at least one cysteine residue in its C-terminal extension. For example, the polypeptide obtainable by or obtained by the methods of the present invention comprises 0-20%, more preferably 0-10%, 0-5%, 0-2% or 0-1% polypeptide lacking the at least one cysteine residue in its C-terminal extension. Most preferably, the polypeptide of the present invention will be free of polypeptide lacking the at least one cysteine residue in its C-terminal extension. The skilled person can readily determine the proportion of polypeptide—as a % of the total—e.g. by Liquid Chromatography (LC) such as RP-HPLC or IE Chromatography or Mass Spectrometry (MS) as described herein.

In view of the absence of polypeptide lacking the at least one cysteine residue in its C-terminal extension, the polypeptide obtainable by or obtained by the method of the present invention is advantageous as compared to prior art preparations. For example, the polypeptide of the present invention will give high yields in coupling with another group, residue or moiety, such as e.g. pegylation.

In a further aspect, the present invention also relates to compounds (also referred to as "compounds of the invention") obtainable by the methods of the present invention as described herein. More particularly, the present invention relates to compounds that comprise a polypeptide of the invention coupled to one or more groups, residues or moieties.

Accordingly, the present invention also relates to compounds obtainable by or obtained by a method comprising the steps of:

d) maintaining a host under conditions that are such that said host expresses and/or produces a polypeptide comprising one ore more variable domains and a C-terminal extension of maximal 10 amino acid residues in which at least one amino acid residue is a cysteine residue;

e) isolating and/or purifying the secreted polypeptide from the medium wherein at least 80% (preferably at least 90%, more preferably at least 95%, most preferably at least 99%) of the polypeptide isolated and/or purified contains the at least one cysteine residue in the C-terminal extension, as determined by mass spectrometry;

f) coupling one or more groups, residues or moieties to the at least one cysteine residue present in the C-terminal extension.

Examples of groups, residues or moieties that can be coupled to the at least one cysteine present in the C-terminal extension will be know to the one skilled in the art and/or are as described herein.

The present invention also relates to pharmaceutical preparations and other compositions comprising the polypeptide and/or compound obtainable by or obtained by the methods of the present invention. The present invention also relates to the diagnostic, prophylactic and/or medical use of the polypeptides and/or compounds obtainable by or obtained by the method of the present invention.

The skilled person can readily formulate pharmaceutically suitable formulations on the basis of common general knowledge. Moreover, the references specifically dealing with (single) domain antibodies and/or Nanobodies, which are cited herein, are explicitly referred to. Without limitation, formulations for standard routes of application can be prepared, including formulations for nasal, oral, intravenous, subcutaneous, intramuscular, intraperitoneal, intravaginal, rectal application, topical application or application by inhalation.

Based on the present invention, the skilled person can also readily devise suitable methods of prevention and/or treatment characterized by the use of a therapeutically effective amount of the compound of the present invention.

Based on the present invention, the skilled person can also readily devise suitable methods of diagnosis characterized by the use of a compound of the present invention. Accordingly, the present invention also relates to diagnostic kits comprising the compound of the present invention.

The invention will now be further described by means of the following non-limiting preferred examples and figures.

EXAMPLES

Example 1

PEGylation of Nanobody 1

A bivalent Nanobody (Nanobody 1-GGGC; SEQ ID NO: 10) was constructed in an expression vector derived from pPICZa (Invitrogen) which contains the AOX1 promoter for tightly regulated, methanol induced expression of Nanobodies in *Pichia pastoris*, a resistance gene for Zeocin™, a multicloning site and the α-factor secretion signal. In frame with the Nanobody coding sequence, the vector codes for a C-terminal GGGC sequence (SEQ ID NO: 1) followed by two stop codons. The bivalent Nanobody was expressed in a recombinant *Pichia pastoris* strain X-33. Purification and PEGylation was carried out as follows: the bivalent Nanobody was purified via Protein A affinity chromatography (MabCapture A (Poros)). After elution, using 100 mM Glycine pH 2.5, the collected sample was immediately neutralized using 1.5M Tris pH7.5, followed by a buffer switch to 1/10 PBS via dialysis using 5DV. After a cation exchange step on a Poros 50HS column (Buffer A: 1/10 PBS—Buffer B: PBS, 1M NaCl pH 7.5) and an additional anion exchange step on a Poros 50HQ column in flow through mode (Buffer A: 25 mM Piperazine pH 10.55—Buffer B: 50 mM Tris pH 7.5 1M NaCl); the fraction containing the bivalent Nanobody was incubated with 10 mM DTT overnight at 4° C. After removal of free DTT by SEC, PEG40 (methoxy polyethylene glycol maleimido-propionamide, average MW=40kDa, Chirotech Technology Ltd.) was added in a 5 molar excess and incubated overnight at 4° C. The PEGylated Nanobody was separated from non-PEGylated Nanobody and free PEG via MacroCap SP cation exchange (Buffer A: 25 mM Na-acetate pH4.5/Buffer B: 25 mM Na-Acetate, 1M NaCl pH 4.5). The bound proteins were eluted with a linear gradient to buffer B, and immediately neutralized using 150 mM Tris pH 7.5. Finally, the PEGylated Nanobody was treated for LPS-removal with 50 mM OGP, which was removed in a final size exclusion using Superdex200pg (GE Healthcare).

Fractions of the MacroCap SP chromatography step (FIG. 1) were analyzed via LDS-page followed by Coomassie brilliant blue staining combined with a PEG staining (FIG. 2).

A high amount (about 50%) of the bivalent Nanobody was not PEGylated, and eluted as a separate peak during the NaCl-gradient elution of the MacroCap SP chromatography step (FIG. 1: fr9-13). Furthermore, this fraction was migrating as a bivalent Nanobody on a SEC_Superdex 75 GL10/30 (FIG. 3_peak 2), and was not stained via PEG-staining yet stains blue via CBB-stain (FIG. 2, lane 12-15). A possible explanation could be either a blocked and/or non-reactive C-terminal—Cys or a loss of the C-terminal—Cys, due to proteolytic cleavage activity during fermentation. To analyze both hypotheses further, an LC/MS analysis was performed on a crude extract form the clarified fermentation broth after a protein A—clean up step and on a mAla-coupled bivalent Nanobody.

Example 2

Biotinylation of the Nanobody 1 and Coupling of the Nanobodies 1 to N-maleoyl-Alanine Bivalent Nanobody (Nanobody 1-GGGC; SEQ ID NO: 10) was constructed in an expression vector derived from pPICZa (Invitrogen) which contains the AOX1 promoter for tightly regulated, methanol induced expression of Nanobodies in *Pichia pastoris*, a resistance gene for Zeocin™, a multicloning site and the a-factor secretion signal. In frame with the Nanobody coding sequence, the vector codes for a C-terminal GGGC sequence (SEQ ID NO: 1) followed by two stop codons. The bivalent Nanobody was expressed in a recombinant *Pichia pastoris* strain X-33. Purification and PEGylation was carried out as follows: the bivalent Nanobody was purified via Protein A affinity chromatography (MabCapture A (Poros)). After elution, using 100 mM Glycine pH 2.5, the collected sample was immediately neutralized using 1.5M Tris pH7.5, followed by a buffer switch to 1/10 PBS via dialysis using 5DV. After a cation exchange step on a Poros 50HS column (Buffer A: 1/10 PBS—Buffer B: PBS, 1M NaCl pH 7.5) and an additional anion exchange step on a Poros 50HQ column in flow through mode (Buffer A: 25 mM Piperazine pH 10.55—Buffer B: 50 mM Tris pH 7.5 1M NaCl); the fraction containing the bivalent Nanobody was incubated with 10 mM DTT overnight at 4° C. After free DTT was removed by SEC, respectively a 5 molar excess of Biotin (EZ-LINK Maleimide-PEO$_2$-Biotin), or N-Maleoyl-alanine (Fluka, ref 63285, lot 13178711; MW=169.14g/mol) were incubated overnight at 4° C. The non-reacted biotin or N-maleoyl-alanine were separated from the cross-linked Nanobody via a Size exclusion chromatography step using Superdex75. The final biotinylated and N-Maleoyl-alanine coupled Nanobodies were analyzed via LDS-page followed by respectively an immunoblotting analysis using an anti-VHH antiserum or by Coomassie brilliant blue staining (FIGS. 4*a* and 4*b*).

Figure 4A:
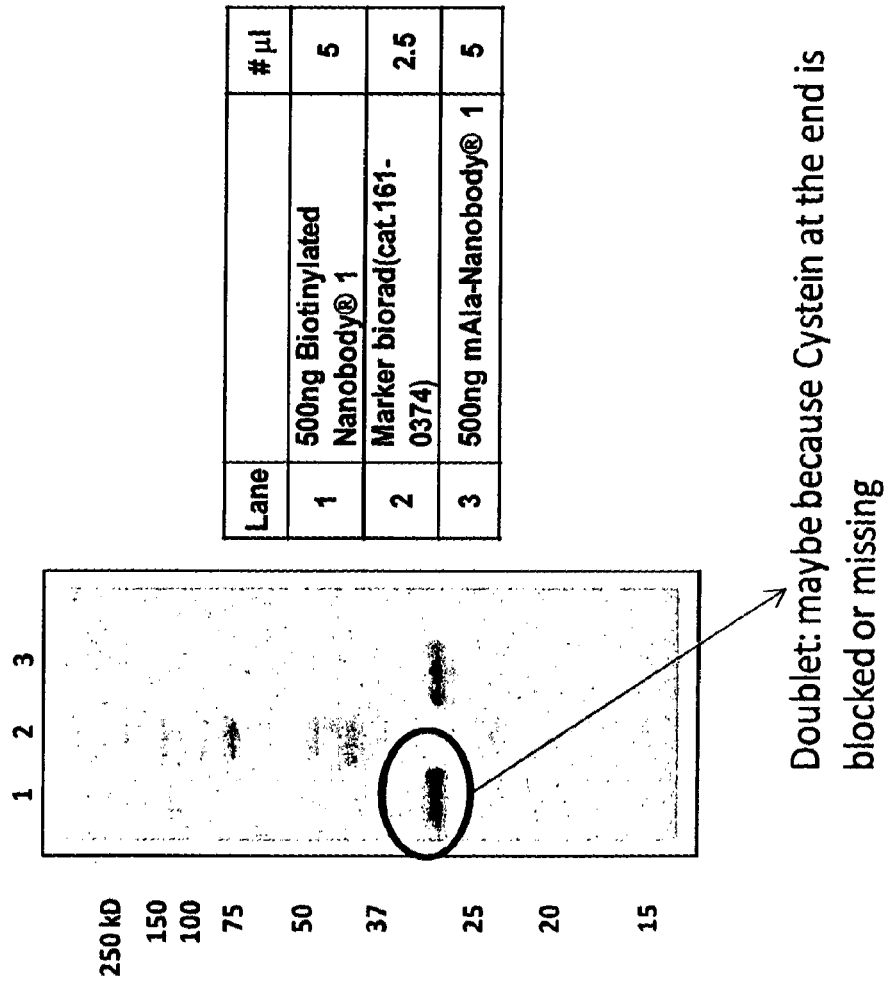
Figure 4B:
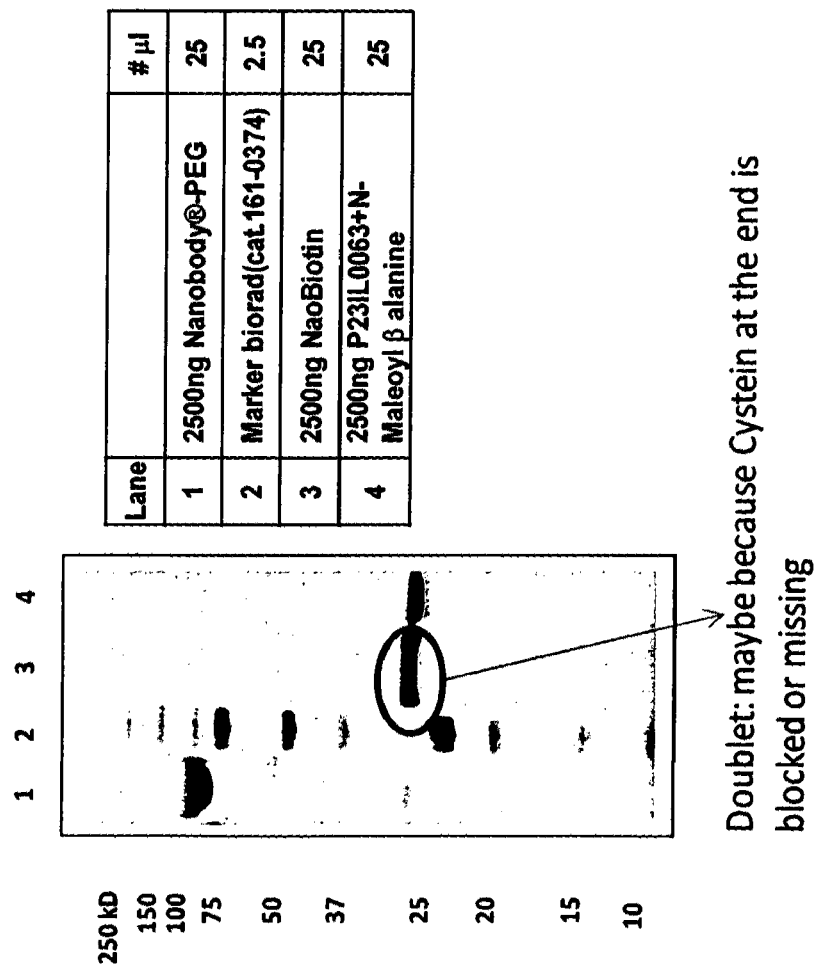

FIG. 4 shows that the biotinylated Nanobody 1 is migrating as a doublet, when detected after immunoblotting using an anti-VHH antiserum or via Coomassie brilliant blue staining (FIGS. 4*a* and 4*b*). This is probably due to the fact that part of the Nanobody (~50%) did not react with Biotin, similar to the PEGylation reaction, and the free Nanobody cannot be separated from the biotinylated Nanobody during the SEC, due to the small difference in size. The reason why the bivalent Nanobody is not reactive and not coupled to Maleimide-PEO2-Biotin could be due to a blocked C-terminal—Cys or due to degradation of the C-terminal—Cys, probably by an exo-protease activity during the fermentation run. LC/MS analysis of the Nanobody 1-Maleoyl-beta-alanine was used to confirm the latter hypothesis. As such, in the total mass spectrum of either the biotinylated Nanobody 1 or the maleoyl-alanine coupled Nanobody 1 batch two peaks were detected, respectively the intact (biotinylated and/or mAla coupled) and the cysteine truncated form (FIGS. 5 and 6).

FIG. 5 shows total LC/MS spectrum of the biotinylated-Nanobody 1 in which two peaks with a different mass were detected. The first detected mass of 29847.8 Da corresponded to the theoretically determined mass of the Nanobody 1-Cystein (29950.9–103.14=29847.8 Da). The second detected mass of 30494.9 Da corresponded to the theoretically determined mass of the protein (Nanobody-1)+maleinimide-PEG2-Biotin (with the maleimide ring opened: 29950.9+525.23+18=30494.1 Da). Based on a peak in the middle of the raw m/z spectrum, both forms were present in following percentages: 29847.8 Da (45%)+30494.9 Da (55%).

FIG. 6 shows LC/MS analysis of maleoyl-alanine coupled Nanobody 1 (purified/and coupled after fermentation at pH3.5). The detected mass of 29847.5 Da corresponded to the theoretically determined mass of the protein (Nanobody-1)–Cysteine (29950.9–103.14=29847.8 Da). The detected mass of 30119.9 Da corresponded to the theoretically determined mass of the protein (Nanobody-1)+N-maleoyl-beta-alanine (29950.9+169=30119.9 Da). Based on a peak in the middle of the raw m/z spectrum, both forms were present in following percentages: 29847.2 Da: 43%+30119.3 Da: 57%.

Example 3

N-Maleoyl Alanine Coupling of Nanobody 2

Bivalent Nanobody (Nanobody 2-GGGC; SEQ ID NO: 12) was constructed in an expression vector derived from pPICZa (Invitrogen) which contains the AOX1 promoter for tightly regulated, methanol induced expression of Nanobodies in *Pichia pastoris*, a resistance gene for Zeocin™, a multicloning site and the a-factor secretion signal. In frame with the Nanobody coding sequence, the vector codes for a C-terminal GGGC sequence (SEQ ID NO: 1) followed by two stop codons. The bivalent Nanobody was expressed in a recombinant *Pichia pastoris* strain X-33, after induction on shake flasks (190mL). Purification and coupling to N-Maleoyl-β-alanine: (Fluka, ref 63285, MW=169.14g/mol) to the bivalent Nanobody was carried out as follows:

Bivalent Nanobody was purified via Protein A affinity chromatography (MabCapture A (Poros)). After elution, using 100 mM Glycine pH 2.6, the collected sample was immediately neutralized using 1.5M Tris pH7.5, followed by a buffer switch to 1/10 PBS via dialysis using 5DV. After a cation exchange step on a Poros 50HS column (Buffer A: 1/10 PBS—Buffer B: PBS, 1M NaCl pH 7.5) and an additional anion exchange step on a Poros 50HQ column in flow through mode (Buffer A: 25 mM Piperazine pH 10.55—Buffer B: 50 mM Tris pH 7.5 1M NaCl); the fraction containing the bivalent Nanobody was incubated with 10 mM DTT over night at 4° C. After free DTT was removed by SEC, respectively a 5 molar excess of N-Maleoyl-alanine (Fluka, ref 63285, lot 1317871; MW=169.14g/mol) was incubated overnight at 4° C. The non-reacted N-maleoyl-alanine was separated from the cross-linked Nanobody via a Size exclusion chromatography step using Superdex75. Next, LC/MS analysis of the Nanobody 2-Maleoyl-beta-alanine demonstrated that approximately 20% of the material was not coupled to N-Maleoyl-β-alanine, because of lack of the free reactive cysteine (FIG. 7). Besides the C-terminal cleavage, no other degradation products were observed. The detected mass of 28027.3 Da corresponded to the theoretically determined mass of the protein (Nanobody-1) –Cysteine. The detected mass of 28299.5 Da corresponded to the theoretically determined mass of the protein (Nanobody-1)+N-maleoyl-beta-alanine.

Example 4

PEGylation of 4 Different Nanobody 1 Variants with Different C-Terminal Extensions Previous experiments have shown that the yield of PEGylation was reduced to 50% due to C-terminal cleavage of the reactive cysteine during production. Therefore new constructs were made with different C-terminal linkers between the Nanobody and the C-terminal cysteine; respectively Nanobody 1-GGC (SEQ ID NO: 12); Nanobody 1-GC (SEQ ID NO: 13); Nanobody 1-C (SEQ ID NO: 14); Nanobody 1-CG (SEQ ID NO: 15); Nanobody 1-AAAC (SEQ ID NO: 16); Nanobody 1-(VVTS)C (SEQ ID NO: 17); Nanobody 1-GGGS (SEQ ID NO: 27). The level of C-terminal cleavage was evaluated via LC/MS analysis after a protein-clean up step, starting form clarified shake flask medium.

For this, two mL of clarified fermentation broth was purified on 200 μL Prot A beads, and eluted with 200 μL 0.1%TFA. This extract was injected on reversed phase chromatography (Zorbax 300SB-C3) directly coupled to mass spectrometry (Q-TOF) for detection. For each chromatographic peak the mass (identity) and its intensity (content) were reported (FIG. 8). In most constructs the intact protein was present under two different forms: one with the c-terminal cysteine coupled to glutathione, and secondly as a dimer by inter disulphide bridge formation: both forms can be reduced (e.g. with DTT) before coupling to PEG. But in each construct with a 3-glycine linker between the framework and the C-terminal cysteine, between 33% and 64% of the material was present without the C-terminal cysteine. In the other constructs, having a slightly different C-terminus, the cysteine-truncation was not detected. In smaller amounts, some other modifications of the protein were also observed.

Next, Nanobody 1-GGGC (SEQ ID NO: 10), together with 5 different C-terminal variants (-GC, -GGC, -GGGCG, -CG, and -C) (SEQ ID NOs: 13, 12, 11, 15 and 14, respectively) were, after fermentation, purified starting from the clarified fermentation broth using Protein A affinity chromatography (POROS). After elution, using 100 mM Glycine pH 2.5, the collected sample was immediately neutralized using 1.5M Tris pH7.5, followed by a buffer switch to 1/10 PBS via dialysis using 5DV. Next, the Nanobodies were incubated with 10 mM DTT over night at 4° C., and after removal of the non-reacted DTT, the reduced Nanobodies were incubated overnight at 4° C. with a 5 molar excess of Biotin (EZ-LINK Maleimide-PEO2-Biotin). The excess of non reacted Biotin was separated from the modified Nanobody via a Size exclusion chromatography step using Superdex75. The purity and the identity of the Nanobody variants coupled to biotin were further analyzed via mass spectrometry (FIG. 9). For all samples the main peak consisted of the intact protein (+maleimide-PEG2-biotin), except for Nanobody 1 with the 3-G linker to the c-terminal cysteine, which also contained approx 25% protein lacking the C-terminal cysteine (and therefore also lacking the maleimide-PEG2-biotin group).

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All references disclosed herein are incorporated by reference, in particular for the teaching that is referenced hereinabove.

Tables

TABLE 1

Sequence of possible C-terminal extensions on single variable domain

| SEQ ID NO: | Sequences |
|---|---|
| 1 | GGGC |
| 2 | GGGCG |
| 3 | GGC |
| 4 | GC |
| 5 | C |
| 6 | CG |
| 7 | AAAC |
| 8 | VTVS*-C |

*C-terminal end of variable domain sequence lacking the final serine (S).

TABLE 2

Sequences of variable domains used in the Example section

| Nanobody | SEQ ID NO: | Sequence |
|---|---|---|
| Nanobody 1 | 9 | EVQLLESGGGLVQPGGSLRLSCAASGRIFSLPASGNIFNLLTIAWYRQAPGKGRE LVATINSGSRTYYADSVKGRFTISRDNSKKTLYLQMNSLRPEDTAVYYCQTSGSG SPNFWGQGTLVTVSSGGGGSGGGGSGGGGSGGGGSGGGGSGGGGSGGGG SEVQLLESGGGLVQPGGSLRLSCAASGLPFSTKSMGWFRQAPGKGREFVSRISP GGTSRYYGDFVKGRFTISRDNSKNTLYLQMNSLRAEDTAVYYCASGERSTYIGSN YYRTNEYDYWGQGTLVTVSS |
| Nanobody 1-GGGC | 10 | EVQLLESGGGLVQPGGSLRLSCAASGRIFSLPASGNIFNLLTIAWYRQAPGKGRE LVATINSGSRTYYADSVKGRFTISRDNSKKTLYLQMNSLRPEDTAVYYCQTSGSG SPNFWGQGTLVTVSSGGGGSGGGGSGGGGSGGGGSGGGGSGGGGSGGGG SEVQLLESGGGLVQPGGSLRLSCAASGLPFSTKSMGWFRQAPGKGREFVSRISP GGTSRYYGDFVKGRFTISRDNSKNTLYLQMNSLRAEDTAVYYCASGERSTYIGSN YYRTNEYDYWGQGTLVTVSSGGGC |
| Nanobody 1-GGGCG | 11 | EVQLLESGGGLVQPGGSLRLSCAASGRIFSLPASGNIFNLLTIAWYRQAPGKGRE LVATINSGSRTYYADSVKGRFTISRDNSKKTLYLQMNSLRPEDTAVYYCQTSGSG SPNFWGQGTLVTVSSGGGGSGGGGSGGGGSGGGGSGGGGSGGGGSGGGG SEVQLLESGGGLVQPGGSLRLSCAASGLPFSTKSMGWFRQAPGKGREFVSRISP GGTSRYYGDFVKGRFTISRDNSKNTLYLQMNSLRAEDTAVYYCASGERSTYIGSN YYRTNEYDYWGQGTLVTVSSGGGCG |

TABLE 2-continued

Sequences of variable domains used in the Example section

| Nanobody | SEQ ID NO: | Sequence |
|---|---|---|
| Nanobody 1-GGC | 12 | EVQLLESGGGLVQPGGSLRLSCAASGRIFSLPASGNIFNLLTIAWYRQAPGKGRE<br>LVATINSGSRTYYADSVKGRFTISRDNSKKTLYLQMNSLRPEDTAVYYCQTSGSG<br>SPNFWGQGTLVTVSSGGGGSGGGGSGGGGSGGGGSGGGGSGGGGSGGGG<br>SEVQLLESGGGLVQPGGSLRLSCAASGLPFSTKSMGWFRQAPGKGREFVSRISP<br>GGTSRYYGDFVKGRFTISRDNSKNTLYLQMNSLRAEDTAVYYCASGERSTYIGSN<br>YYRTNEYDYWGQGTLVTVSSGGC |
| Nanobody 1-GC | 13 | EVQLLESGGGLVQPGGSLRLSCAASGRIFSLPASGNIFNLLTIAWYRQAPGKGRE<br>LVATINSGSRTYYADSVKGRFTISRDNSKKTLYLQMNSLRPEDTAVYYCQTSGSG<br>SPNFWGQGTLVTVSSGGGGSGGGGSGGGGSGGGGSGGGGSGGGGSGGGG<br>SEVQLLESGGGLVQPGGSLRLSCAASGLPFSTKSMGWFRQAPGKGREFVSRISP<br>GGTSRYYGDFVKGRFTISRDNSKNTLYLQMNSLRAEDTAVYYCASGERSTYIGSN<br>YYRTNEYDYWGQGTLVTVSSGC |
| Nanobody 1-C | 14 | EVQLLESGGGLVQPGGSLRLSCAASGRIFSLPASGNIFNLLTIAWYRQAPGKGRE<br>LVATINSGSRTYYADSVKGRFTISRDNSKKTLYLQMNSLRPEDTAVYYCQTSGSG<br>SPNFWGQGTLVTVSSGGGGSGGGGSGGGGSGGGGSGGGGSGGGGSGGGG<br>SEVQLLESGGGLVQPGGSLRLSCAASGLPFSTKSMGWFRQAPGKGREFVSRISP<br>GGTSRYYGDFVKGRFTISRDNSKNTLYLQMNSLRAEDTAVYYCASGERSTYIGSN<br>YYRTNEYDYWGQGTLVTVSSC |
| Nanobody 1-CG | 15 | EVQLLESGGGLVQPGGSLRLSCAASGRIFSLPASGNIFNLLTIAWYRQAPGKGRE<br>LVATINSGSRTYYADSVKGRFTISRDNSKKTLYLQMNSLRPEDTAVYYCQTSGSG<br>SPNFWGQGTLVTVSSGGGGSGGGGSGGGGSGGGGSGGGGSGGGGSGGGG<br>SEVQLLESGGGLVQPGGSLRLSCAASGLPFSTKSMGWFRQAPGKGREFVSRISP<br>GGTSRYYGDFVKGRFTISRDNSKNTLYLQMNSLRAEDTAVYYCASGERSTYIGSN<br>YYRTNEYDYWGQGTLVTVSSCG |
| Nanobody 1-AAAC | 16 | EVQLLESGGGLVQPGGSLRLSCAASGRIFSLPASGNIFNLLTIAWYRQAPGKGRE<br>LVATINSGSRTYYADSVKGRFTISRDNSKKTLYLQMNSLRPEDTAVYYCQTSGSG<br>SPNFWGQGTLVTVSSGGGGSGGGGSGGGGSGGGGSGGGGSGGGGSGGGG<br>SEVQLLESGGGLVQPGGSLRLSCAASGLPFSTKSMGWFRQAPGKGREFVSRISP<br>GGTSRYYGDFVKGRFTISRDNSKNTLYLQMNSLRAEDTAVYYCASGERSTYIGSN<br>YYRTNEYDYWGQGTLVTVSSAAAC |
| Nanobody 1-(VTVS)C | 17 | EVQLLESGGGLVQPGGSLRLSCAASGRIFSLPASGNIFNLLTIAWYRQAPGKGRE<br>LVATINSGSRTYYADSVKGRFTISRDNSKKTLYLQMNSLRPEDTAVYYCQTSGSG<br>SPNFWGQGTLVTVSSGGGGSGGGGSGGGGSGGGGSGGGGSGGGGSGGGG<br>SEVQLLESGGGLVQPGGSLRLSCAASGLPFSTKSMGWFRQAPGKGREFVSRISP<br>GGTSRYYGDFVKGRFTISRDNSKNTLYLQMNSLRAEDTAVYYCASGERSTYIGSN<br>YYRTNEYDYWGQGTLVTVSC |
| Nanobody 2 | 18 | DVQLVESGGGLVQPGGSLRLSCAASGRTFSYNPMGWFRQAPGKGRELVAAIS<br>RTGGSTYYPESVEGRFTISRDNAKRTVYLQMNSLRAEDTAVYYCAAAGVRAEQ<br>GRVRTLPSEYTFWGQGTQVTVSSAAAEVQLVESGGGLVQPGGSLRLSCAASGR<br>TFSYNPMGWFRQAPGKGRELVAAISRTGGSTYYPESVEGRFTISRDNAKRTVYL<br>QMNSLRAEDTAVYYCAAAGVRAEQGRVRTLPSEYTFWGQGTQVTVSS |
| Nanobody 2-GGGC | 19 | DVQLVESGGGLVQPGGSLRLSCAASGRTFSYNPMGWFRQAPGKGRELVAAIS<br>RTGGSTYYPESVEGRFTISRDNAKRTVYLQMNSLRAEDTAVYYCAAAGVRAEQ<br>GRVRTLPSEYTFWGQGTQVTVSSAAAEVQLVESGGGLVQPGGSLRLSCAASGR<br>TFSYNPMGWFRQAPGKGRELVAAISRTGGSTYYPESVEGRFTISRDNAKRTVYL<br>QMNSLRAEDTAVYYCAAAGVRAEQGRVRTLPSEYTFWGQGTQVTVSSGGGC |
| Nanobody 2-GGGCG | 20 | DVQLVESGGGLVQPGGSLRLSCAASGRTFSYNPMGWFRQAPGKGRELVAAIS<br>RTGGSTYYPESVEGRFTISRDNAKRTVYLQMNSLRAEDTAVYYCAAAGVRAEQ<br>GRVRTLPSEYTFWGQGTQVTVSSAAAEVQLVESGGGLVQPGGSLRLSCAASGR<br>TFSYNPMGWFRQAPGKGRELVAAISRTGGSTYYPESVEGRFTISRDNAKRTVYL<br>QMNSLRAEDTAVYYCAAAGVRAEQGRVRTLPSEYTFWGQGTQVTVSSGGGC<br>G |
| Nanobody 2-GGC | 21 | DVQLVESGGGLVQPGGSLRLSCAASGRTFSYNPMGWFRQAPGKGRELVAAIS<br>RTGGSTYYPESVEGRFTISRDNAKRTVYLQMNSLRAEDTAVYYCAAAGVRAEQ<br>GRVRTLPSEYTFWGQGTQVTVSSAAAEVQLVESGGGLVQPGGSLRLSCAASGR<br>TFSYNPMGWFRQAPGKGRELVAAISRTGGSTYYPESVEGRFTISRDNAKRTVYL<br>QMNSLRAEDTAVYYCAAAGVRAEQGRVRTLPSEYTFWGQGTQVTVSSGGC |
| Nanobody 2-GC | 22 | DVQLVESGGGLVQPGGSLRLSCAASGRTFSYNPMGWFRQAPGKGRELVAAIS<br>RTGGSTYYPESVEGRFTISRDNAKRTVYLQMNSLRAEDTAVYYCAAAGVRAEQ<br>GRVRTLPSEYTFWGQGTQVTVSSAAAEVQLVESGGGLVQPGGSLRLSCAASGR<br>TFSYNPMGWFRQAPGKGRELVAAISRTGGSTYYPESVEGRFTISRDNAKRTVYL<br>QMNSLRAEDTAVYYCAAAGVRAEQGRVRTLPSEYTFWGQGTQVTVSSGC |
| Nanobody 2-C | 23 | DVQLVESGGGLVQPGGSLRLSCAASGRTFSYNPMGWFRQAPGKGRELVAAIS<br>RTGGSTYYPESVEGRFTISRDNAKRTVYLQMNSLRAEDTAVYYCAAAGVRAEQ<br>GRVRTLPSEYTFWGQGTQVTVSSAAAEVQLVESGGGLVQPGGSLRLSCAASGR |

TABLE 2-continued

Sequences of variable domains used in the Example section

| Nanobody | SEQ ID NO: | Sequence |
|---|---|---|
| | | TFSYNPMGWFRQAPGKGRELVAAISRTGGSTYYPESVEGRFTISRDNAKRTVYL<br>QMNSLRAEDTAVYYCAAAGVRAEQGRVRTLPSEYTFWGQGTQVTVSSC |
| Nanobody 2-CG | 24 | DVQLVESGGGLVQPGGSLRLSCAASGRTFSYNPMGWFRQAPGKGRELVAAIS<br>RTGGSTYYPESVEGRFTISRDNAKRTVYLQMNSLRAEDTAVYYCAAAGVRAEQ<br>GRVRTLPSEYTFWGQGTQVTVSSAAAEVQLVESGGGLVQPGGSLRLSCAASGR<br>TFSYNPMGWFRQAPGKGRELVAAISRTGGSTYYPESVEGRFTISRDNAKRTVYL<br>QMNSLRAEDTAVYYCAAAGVRAEQGRVRTLPSEYTFWGQGTQVTVSSCG |
| Nanobody 2-AAAC | 25 | DVQLVESGGGLVQPGGSLRLSCAASGRTFSYNPMGWFRQAPGKGRELVAAIS<br>RTGGSTYYPESVEGRFTISRDNAKRTVYLQMNSLRAEDTAVYYCAAAGVRAEQ<br>GRVRTLPSEYTFWGQGTQVTVSSAAAEVQLVESGGGLVQPGGSLRLSCAASGR<br>TFSYNPMGWFRQAPGKGRELVAAISRTGGSTYYPESVEGRFTISRDNAKRTVYL<br>QMNSLRAEDTAVYYCAAAGVRAEQGRVRTLPSEYTFWGQGTQVTVSSAAAC |
| Nanobody 2-(VTVS)C | 26 | DVQLVESGGGLVQPGGSLRLSCAASGRTFSYNPMGWFRQAPGKGRELVAAIS<br>RTGGSTYYPESVEGRFTISRDNAKRTVYLQMNSLRAEDTAVYYCAAAGVRAEQ<br>GRVRTLPSEYTFWGQGTQVTVSSAAAEVQLVESGGGLVQPGGSLRLSCAASGR<br>TFSYNPMGWFRQAPGKGRELVAAISRTGGSTYYPESVEGRFTISRDNAKRTVYL<br>QMNSLRAEDTAVYYCAAAGVRAEQGRVRTLPSEYTFWGQGTQVTVTVSC |
| Nanobody 1-GGGS | 27 | EVQLLESGGGLVQPGGSLRLSCAASGRIFSLPASGNIFNLLTIAWYRQAPGKGRE<br>LVATINSGSRTYYADSVKGRFTISRDNSKKTLYLQMNSLRPEDTAVYYCQTSGSG<br>SPNFWGQGTLVTVSSGGGGSGGGGSGGGGSGGGGSGGGGSGGGGSGGGG<br>SEVQLLESGGGLVQPGGSLRLSCAASGLPFSTKSMGWFRQAPGKGREFVSRISP<br>GGTSRYYGDFVKGRFTISRDNSKNTLYLQMNSLRAEDTAVYYCASGERSTYIGSN<br>YYRTNEYDYWGQGTLVTVSSGGGS |

The invention claimed is:

1. A method for the expression and/or production of a polypeptide comprising one or more immunoglobulin single variable domains linked to a C-terminal extension, said method comprising the steps of:
   a) maintaining a host under conditions that are such that said host expresses and/or produces the polypeptide;
   b) isolating and/or purifying the polypeptide from culture medium in which said host cell was cultivated;
   wherein the C-terminal extension is selected from any one of SEQ ID NOs: 2-4 and 6-7; and
   wherein at least 80% of the polypeptide isolated and/or purified in step b) contains the C-terminal extension, as determined by mass spectrometry.

2. A method according to claim 1, wherein at least 90% of the polypeptide isolated and/or purified in step b) contains the C-terminal extension, as determined by mass spectrometry.

3. A method according to claim 2, wherein at least 95% of the polypeptide isolated and/or purified in step b) contains the C-terminal extension, as determined by mass spectrometry.

4. A method according to claim 3, wherein at least 99% of the polypeptide isolated and/or purified in step b) contains the C-terminal extension, as determined by mass spectrometry.

5. A method according to claim 1, wherein said host cell is selected from prokaryotic hosts or eukaryotic hosts cells.

6. A method according to claim 5, wherein said eukaryotic host cell is selected from insect cells, mammalian cells, and lower eukaryotic cells.

7. A method according to claim 1, comprising the further step of coupling one or more groups, residues or moieties to a cysteine residue present in the C-terminal extension.

8. A method according to claim 7, wherein said one or more groups, residues or moieties are selected from polyethylene glycol (PEG), a peptide, a small molecule drug, a lipid and a radiolabelled molecule.

9. A method according to claim 1, wherein the one or more single variable domains is a light chain variable domain sequence or a heavy chain variable domain sequence.

10. A method according to claim 9, wherein the one or more immunoglobulin single variable domains is one or more domain antibodies or one or more Nanobodies.

11. A method according to claim 10, wherein the one or more immunoglobulin single variable domains is one or more VHHs, one or more humanized VHHs, or one or more camelized VHs.

12. A method according to claim 5, wherein said eukaryotic host cell is selected from *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus*, or *Endomycopsis*.

13. A method according to claim 5, wherein said eukaryotic host cell is *Pichia pastoris*.

14. An isolated nucleic acid comprising a nucleotide sequence that encodes a polypeptide comprising one or more immunoglobulin single variable domains linked to a C-terminal extension wherein the C-terminal extension is selected from any one of SEQ ID NOs: 2-4 and 6-7.

15. An isolated nucleic acid according to claim 14, which is in the form of a genetic construct.

16. An isolated host cell that comprises a nucleic acid according to claim 14.

* * * * *

UNITED STATES PATENT AND TRADEMARK OFFICE
CERTIFICATE OF CORRECTION

PATENT NO. : 9,150,640 B2
APPLICATION NO. : 13/382561
DATED : October 6, 2015
INVENTOR(S) : Hilde Stals et al.

Page 1 of 1

It is certified that error appears in the above-identified patent and that said Letters Patent is hereby corrected as shown below:

In the Claims:

Claim 1, column 59, line 14, should read:

1. A method for the expression and/or production of a polypeptide comprising one or more immunoglobulin single variable domains linked to a C-terminal extension, said method comprising the steps of:

a) maintaining a host cell under conditions that are such that said host cell expresses and/or produces the polypeptide;

b) isolating and/or purifying the polypeptide from culture medium in which said host cell was cultivated;

wherein the C-terminal extension is selected from any one of SEQ ID NOs: 2-4 and 6-7; and wherein at least 80 % of the polypeptide isolated and/or purified in step b) contains the C-terminal extension, as determined by mass spectrometry.

Claim 5, column 59, line 37, should read:

5. A method according to claim 1, wherein said host cell is selected from prokaryotic host cells or eukaryotic host cells.

Claim 14, column 60, line 35, should read:

14. An isolated nucleic acid comprising a nucleotide sequence that encodes a polypeptide comprising one or more immunoglobulin single variable domains linked to a C-terminal extension, wherein the C-terminal extension is selected from any one of SEQ ID NOs: 2-4 and 6-7.

Signed and Sealed this
Sixteenth Day of August, 2016

Michelle K. Lee
*Director of the United States Patent and Trademark Office*